(12) United States Patent
Ettenhofer et al.

(10) Patent No.: US 11,426,069 B2
(45) Date of Patent: Aug. 30, 2022

(54) ENHANCED NEUROPSYCHOLOGICAL ASSESSMENT WITH EYE TRACKING

(71) Applicant: The Henry M. Jackson Foundation for the Advancement of Military Medicine, Inc., Bethesda, MD (US)

(72) Inventors: Mark L. Ettenhofer, Silver Spring, MD (US); David Barry, Rockville, MD (US)

(73) Assignee: The Henry M. Jackson Foundation for the Advancement of Military Medicine, Inc., Bethesda, MD (US)

( * ) Notice: Subject to any disclaimer, the term of this patent is extended or adjusted under 35 U.S.C. 154(b) by 1022 days.

(21) Appl. No.: 14/773,987

(22) PCT Filed: Mar. 10, 2014

(86) PCT No.: PCT/US2014/022468
§ 371 (c)(1),
(2) Date: Oct. 1, 2015

(87) PCT Pub. No.: WO2014/164453
PCT Pub. Date: Oct. 9, 2014

(65) Prior Publication Data
US 2016/0022136 A1 Jan. 28, 2016

Related U.S. Application Data

(60) Provisional application No. 61/779,801, filed on Mar. 13, 2013.

(51) Int. Cl.
*A61B 3/113* (2006.01)
*A61B 5/16* (2006.01)
(Continued)

(52) U.S. Cl.
CPC ............ *A61B 3/113* (2013.01); *A61B 5/1104* (2013.01); *A61B 5/162* (2013.01); *A61B 5/165* (2013.01);
(Continued)

(58) Field of Classification Search
CPC ....... A61B 3/113; A61B 5/1104; A61B 5/162; A61B 5/165; A61B 5/168; A61B 5/4076;
(Continued)

(56) References Cited

U.S. PATENT DOCUMENTS 6,231,187 B1    5/2001  Munoz et al.
2008/0104415 A1*  5/2008  Palti-Wasserman .... G06F 21/32
                                                        713/186

(Continued)

FOREIGN PATENT DOCUMENTS

WO    WO 00/72745 A1    12/2000
WO    WO 2006/029021 A2    3/2006
(Continued)

OTHER PUBLICATIONS

International Search Report dated Jul. 30, 2014 in application No. PCT/US2014/022468.
(Continued)

*Primary Examiner* — Daniel L Cerioni
(74) *Attorney, Agent, or Firm* — Foley & Lardner LLP

(57) ABSTRACT

Provided are methods and system for assessing a human subject's neurological and/or psychological status. The methods entail displaying visual tests to a human subject, wherein each of the visual tests includes a visual target signal, optionally with visual cue signals, for eliciting visual and, optionally, body part, movements by the subject. Following the display, the movements are then detected. The latency and/or correctness of such movements can then be used to assess the subject's neurological and/or psychologi-
(Continued)

cal status. Also provided are methods and systems for assessing performance validity.

24 Claims, 6 Drawing Sheets

(51) Int. Cl.
*A61B 5/00* (2006.01)
*A61B 5/11* (2006.01)
*G16H 50/20* (2018.01)

(52) U.S. Cl.
CPC ............ *A61B 5/168* (2013.01); *A61B 5/4076* (2013.01); *A61B 5/4845* (2013.01); *A61B 5/4848* (2013.01); *A61B 5/4884* (2013.01); *A61B 5/7221* (2013.01); *G16H 50/20* (2018.01); *A61B 5/4082* (2013.01); *A61B 5/4094* (2013.01); *A61B 5/742* (2013.01); *A61B 5/7475* (2013.01); *A61B 2503/20* (2013.01)

(58) Field of Classification Search
CPC ... A61B 5/4845; A61B 5/4848; A61B 5/4884; A61B 5/7221; G16H 50/20
USPC ........................................................ 600/558
See application file for complete search history.

(56) References Cited

U.S. PATENT DOCUMENTS

| | | | |
|---|---|---|---|
| 2010/0092929 A1* | 4/2010 | Hallowell | G09B 5/06 434/167 |
| 2010/0100001 A1 | 4/2010 | Aguilar et al. | |
| 2011/0065076 A1 | 3/2011 | Duffy | |
| 2011/0066070 A1* | 3/2011 | Duffy | A61B 5/16 600/558 |
| 2011/0109879 A1 | 5/2011 | Palti-Wasserman et al. | |
| 2011/0175932 A1 | 7/2011 | Yu et al. | |
| 2012/0320336 A1 | 12/2012 | Kapoula et al. | |
| 2012/0330178 A1 | 12/2012 | Kraft et al. | |

FOREIGN PATENT DOCUMENTS

| | | |
|---|---|---|
| WO | WO 2006/061833 A2 | 6/2006 |
| WO | WO 2012/135654 A1 | 10/2012 |

OTHER PUBLICATIONS

Supplementary European Search Report dated Nov. 16, 2016 in application No. EP 14 78 0396.

* cited by examiner

A

D

B

E

C

F

ENHANCED NEUROPSYCHOLOGICAL ASSESSMENT WITH EYE TRACKING

CROSS-REFERENCE TO RELATED APPLICATIONS

This application is the U.S. national stage of application number PCT/US2014/022468, filed on Mar. 10, 2014, which claims the benefit under 35 U.S.C. § 119(e) to U.S. provisional application Ser. No. 61/779,801, filed Mar. 13, 2013, the contents of which are incorporated here by reference in their entirety.

STATEMENT REGARDING FEDERALLY SPONSORED RESEARCH OR DEVELOPMENT

This invention was made with government support under Intramural Grant R072LP awarded by the Uniformed Services University. The government has certain rights in the invention.

FIELD

The present disclosure generally relates to systems, devices and methods for assessing a human subject's neurological and/or psychological status. The systems, devices and methods also are useful for diagnosis of neurocognitive disorders.

BACKGROUND

Neurocognitive performance can be affected by a wide range of factors, including pre-existing strengths and weaknesses, clinical conditions such as brain injury or dementia, temporary fluctuations in stress or fatigue and other neurological and/or psychological conditions. However, existing assessment tools are often unable to detect the impact of subtle cognitive impairments, and they often produce false positives due to co-morbid psychological health issues. Additionally, these measures are susceptible to the effects of poor effort due to malingering or self-handicapping on baseline testing in an effort to "stay in the game" after future injuries.

Eye tracking technology provides a new opportunity to address these limitations. Research has shown that many neurological and/or psychological conditions are associated with abnormal eye movements. However, the basic, one-dimensional eye tracking measures that are currently available provide insufficient information to distinguish between multiple possible causes of impairment, and are therefore susceptible to false positives.

SUMMARY

Accordingly, the present disclosure provides, in one embodiment, a system comprising a processor and program code which, when executed by the processor, configures the system to conduct an assessment of the neurological and/or psychological status of a subject comprising: displaying a plurality of visual tests to a human subject, wherein each visual test comprises a visual target signal associated with a commanded eye movement and, optionally, a commanded body part movement; detecting, following the display of each visual target signal, a responsive eye movement of the subject and, optionally, a responsive body part movement of the subject; and assessing the neurological and/or psychological status of the subject based on one or more of the latency and correctness of the responsive movements with regard to the commanded movements associated with each visual test.

In some embodiments, the correctness of a responsive movement is determined with reference to its correlation with the visual target signal of the visual test.

In some embodiments, one or more of the visual tests further comprises a visual cue signal displayed prior to the visual target signal. In some embodiments, the visual cue signal is selected from the group consisting of nondirectional cue signals, directional cue signals, misdirectional cue signals, inhibition cue signals, fixation cue signals, and uncued gap signals. In some embodiments, the correctness of a responsive movement is determined with reference to its correlation with the visual target signal as modified by the visual clue signal of the visual test.

In any embodiments, the system may be further configured to detect fixation of the subject's gaze on the visual target signal of the visual test. In some embodiments, the system is further configured to move the visual target signal and detect whether the subject's eye movement tracks the movement of the visual target signal.

In any embodiments, the system may be configured to provide a rest interval between subsequent visual tests.

In any embodiments, the detected eye movement may comprise horizontal and/or vertical movement. In some embodiments, the detected eye movement comprises dilation or constriction. In some embodiments, the detected body part movement comprises one or more movements selected from the group consisting of pressing a button, turning a steering wheel, moving a joystick, depressing a pedal and making a sound.

In any embodiments, the assessment may be based on one or more of the latency of the movements, the correctness of the eye movements with regard to the commanded eye movements, the correctness of the body part movements with regard to the commanded body part movements, and the coordination between the eye and body part movements. In some embodiments, the assessment is based on the subject's performance on a plurality of visual tests.

In any embodiments, the program code may further configure the system to provide an output based on the detected movements, such as numerical output, graphical output, visual output, and textual output.

In any embodiments, the program code may further configure the system to exclude from the determination a confounding non-responsive movement, such as may be associated with eye blinks, excessive body movement, the subject being unprepared for the visual test, the subject being distracted, and a hardware loss of signal.

In any embodiments, the program code may further configure the system during the assessment to automatically recalibrate to compensate for changes in head position during the assessment.

In any embodiments, the program code may further configure the system to monitor the subject's readiness to respond to a visual test and, optionally, pause an assessment, recalibrate, provide instructions to the subject, and/or issue a warning to the subject.

In any embodiments, the program code may configure the system to assess the neurological and/or psychological status of the subject with further reference to historic performance of the subject on a previous assessment.

In any embodiments, the program code may configure the system to assess the neurological and/or psychological status of the subject with further reference to a normative database of movements of a comparable subject population.

In any embodiments, the program code may further configure the system to determine whether the subject's performance is affected by a confounding condition, such as one selected from the group consisting of fatigue, stress, depression, combat exposure, dissimulation, intoxication, effect of medication, and low motivation, based on the subject's performance on a plurality of visual tests.

In any embodiments, the program code may configure the system to assess the neurological and/or psychological status of the subject with further reference to the subject's performance validity on the assessment.

In any embodiments, the program code may configure the system to detect a non-responsive eye movement, wherein the assessment is further based on the non-responsive eye movement.

In any embodiments, the system may further comprise a sensor for detecting one or more of vertical and horizontal movement of the eye and dilation or constriction of the pupil. In some embodiments, the system further comprises a sensor for detecting the movement of the body part.

In any embodiments, the neurological and/or psychological status may be selected from the group consisting of concussion, brain injury, ADHD, dementia, HIV-associated neurocognitive disorders, stroke, Parkinson's disease, multiple sclerosis, brain tumor, hypoxia, hydrocephalus, seizure disorder, brain infection, Huntington's Disease, learning disabilities, cerebrovascular disease, toxic exposure, depression, anxiety, post-traumatic stress disorder (PTSD), traumatic brain injury (TBI).

Also provided, in one embodiment, is a non-transitory computer-readable media comprising program code which, when executed, configures a system to: display a plurality of visual tests to a human subject, wherein each visual test comprises a visual target signal associated with a commanded eye movement and, optionally, a commanded body part movement; detect, following the display of each visual target signal, a responsive eye movement of the subject and, optionally, a responsive body part movement of the subject; and assess the neurological and/or psychological status of the subject based on the latency and/or correctness of the responsive movements with regard to the commanded movements associated with each visual test.

Provided, in another embodiment, is a method for conducting an assessment of the neurological and/or psychological status of a human subject, comprising: displaying, on an electronic screen, a plurality of visual tests to a human subject, wherein each visual test comprises a visual target signal associated with a commanded eye movement and, optionally, a commanded body part movement; detecting, following the display of each visual target signal, a responsive eye movement of the subject and, optionally, a responsive body part movement of the subject; and assessing the neurocognitive function of the subject based on the latency and/or correctness of the responsive movements with regard to the commanded movements associated with each visual test.

In some embodiments, the method comprises a practice stage and a test stage. Additionally or alternatively, in some embodiments, the method further comprises detecting fixation of the subject's gaze on the visual target signal of the visual test. Additionally or alternatively, in some embodiments, the method further comprises moving the visual target signal and detecting whether the subject's eye movement tracks the movement of the visual target signal. In some embodiments, the method further comprises detecting a non-responsive eye movement.

In any embodiments, one or more of the visual tests may further comprise a visual cue signal displayed prior to the visual target signal.

In any embodiments, the visual cue signal may be selected from the group consisting of nondirectional cue signals, directional cue signals, misdirectional cue signals, inhibition cue signals, fixation cue signals, and uncued gap signals.

In any embodiments, the method may comprise adjusting the duration of the time during which a visual signal is displayed based on information regarding the subject's performance during the assessment.

In any embodiments, the method may comprise adjusting the duration of the time between visual signals based on information regarding the subject's performance during the assessment.

In any embodiments, the method may further comprise comparing the subject's performance on the assessment to the subject's performance on a previous assessment or to a normative database.

In yet another embodiment, provided is a system comprising a processor and program code which, when executed by the processor, configures the system to conduct an assessment of the validity of a subject's performance on a visual test comprising: displaying a visual test to a human subject; and assessing the validity of the subject's performance on the visual test based on one or more of a responsive eye movement, a non-responsive eye movement, and an involuntary eye movement, and optionally, one or more of a responsive body movement, a non-responsive body movement, and an involuntary body movement.

In some embodiments, the program code further configures the system to compare the subject's performance to the subject's performance on a previous assessment or to a normative database of performance.

BRIEF DESCRIPTION OF THE DRAWINGS

The figures of the accompanying drawings describe embodiments by way of illustration and not limitation, in which.

Figure 1:
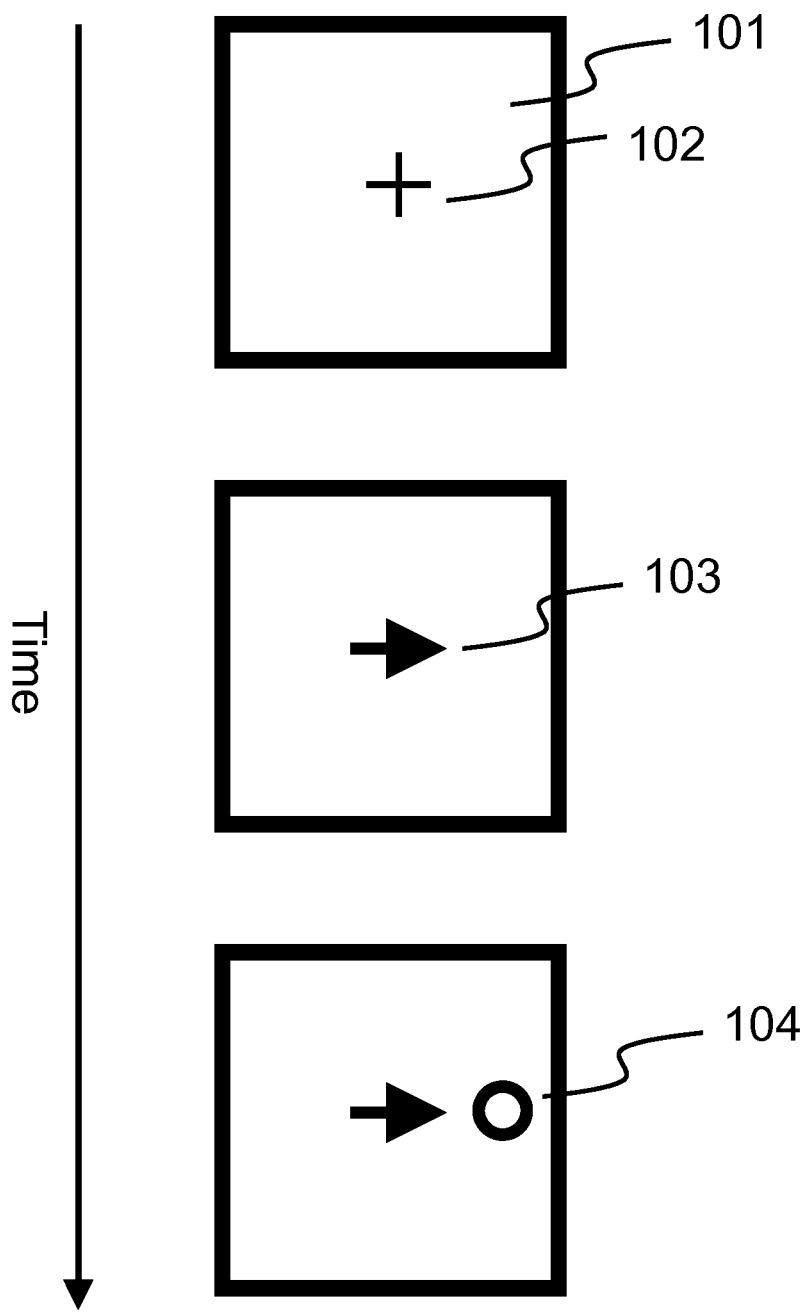
FIG. 1 illustrates a series of visual tests, each of which contains one or more visual signals, that may be sequentially displayed to a test subject during a neuropsychological assessment.

It will be recognized that some or all of the figures are schematic representations for exemplification and, hence, that they do not necessarily depict the actual relative sizes or locations of the elements shown.

DETAILED DESCRIPTION

Certain terms employed in this description have the following defined meanings. Terms that are not defined have their art-recognized meanings. That is, unless otherwise defined, all technical and scientific terms used herein have the same meaning as commonly understood by one of ordinary skill in the art to which this invention belongs.

As used herein, the singular form "a", "an" and "the" include plural references unless the context clearly dictates otherwise.

As used herein, the term "comprising" is intended to mean that the systems, devices and/or methods include the recited components or steps, and also may include others. "Consisting essentially of" means that the systems, devices and/or methods include the recited components or steps, and also may include others, but do not include other components or steps that would materially affect the basic and novel characteristics of the systems, devices and/or methods. In general, the disclosure includes embodiments that comprise, consist essentially of or consist of the described components or steps.

As used herein, the term "subject" refers to any human, including a healthy human, a human diagnosed with or at risk of a neurological and/or psychological condition or disorder, a human being monitored for or undergoing treatment for a neurological and/or psychological condition or disorder, or a human whose neurological and/or psychological status is being assessed or monitored for any reason.

The present disclosure provides systems, methods and devices that display visual signals to a subject to elicit visual (ocular) and, optionally, body part (e.g., hand, finger, leg, foot or other body part, including vocal chord movements to make a sound) movements from the subject and detect the subject's responsive movements. In accordance with some embodiments, detecting both visual and body part movements permits a more accurate and robust assessment of the subject's neurological and/or psychological status. Further, in accordance with such embodiments, the visual signals and corresponding movements can be designed such that responses are indicative of multiple neurocognitive processes such as vigilance, inhibition, conflict resolution, basic perceptual speed, and effort. In specific embodiments, data related to the visual signals and subject movements are processed to account for non-responsive movements.

The present disclosure also provides systems, methods and devices for assessing performance validity of a subject's performance on a visual test that comprise detecting the subject's eye movements and, optionally, body part movements, and correlating such movements with performance validity.

A. Visual and Body Part Movements

Eye movements occur quickly. By comparison, body part movements, even as simple as a finger click, take substantially more time. Responses that occur more rapidly are typically more "automatic" and therefore are less influenced by a subject's conscious thoughts or intentions. This is consistent with the fact that humans are not consciously aware of many of our eye movements, which serve to provide information of interest from the visual environment. As such, eye movements provide a moment-to-moment reflection of a subject's visual attention, usually with minimal interference from other factors. Such visual attention is supported, at least in part, by the brain system.

By contrast, body part movements, such as the intentional movement of an arm, finger, leg or toe or making a sound, occur less quickly in response to a stimulus, and are more susceptible to influence by manipulation of the stimulus and/or alterations in neurological and/or psychological status.

In some embodiments, both ocular and body part movements are detected in response to a visual test, thereby providing more insight into a subject's neurological/psychological status. Such embodiments are more sensitive and robust than one-dimensional eye-tracking, and can distinguish between neurocognitive deficits related to factors such as brain injury, traumatic stress, depression, or poor effort. These advantages stem both from having both sets of data and also from being able to compare and correlate eye movement and body part movements A "visual" or "ocular" response, as used herein, refers to the movement of one or both eyes of a human subject in response to the display of a visual signal. Therefore, a visual response also is referred to herein as a "responsive eye movement" or simply an "eye movement." In some aspects, the subject has been instructed to follow certain rules when a given visual signal is displayed, such as moving the eyes towards a direction or a target indicated by the visual signal, or in an opposite or different direction. In some embodiments, the subject has not been given specific instructions, but nevertheless exhibits eye movements responsive to the visual signals. Detection of a visual response can include multiple parameters, such as latency and correctness, as further described below.

A "manual response" or a "responsive movement of a body part," as used herein, refers to the movement of a body part, such as a hand, finger, leg, etc., of a human subject in response to the display of a visual signal. Therefore, a manual response also is referred to herein as a "responsive body part movement" or simply a "body part movement." In some aspects, the subject has been instructed to follow certain rules when viewing the visual signals, such as clicking on a button, turning a wheel, or pressing a pedal in response to a given visual signal. Detection of a manual response can include multiple parameters, such as latency and correctness, also described in more detail below.

A "non-responsive movement" as used herein (whether a non-responsive eye movement or a non-responsive body part movement) refers to any movement that is not made in response to a signal, including voluntary movements and involuntary movements.

A.1 Types of Visual Signals

The present invention includes systems, devices and methods that involve displaying a series of visual tests to a subject, wherein at least one of the visual tests includes a visual signal associated with both a commanded eye movement and a commanded body part movement.

A "visual test," as used herein, refers to the collection of one or more visual signals that are displayed concurrently or sequentially to command an eye and/or a body part movement from a human subject to whom the visual test is displayed. As discussed in more detail below, a visual test may include a "visual target signal" associated with commanded movements and, optionally, a visual cue signal. As discussed in more detail below, a "visual cue signal" may provide information about the timing or location of the subsequent (e.g., upcoming) visual target signal and/or may provide information about the commanded movement associated with the upcoming visual target signal, including that the subject should not perform a movement. In some embodiments, a visual test also may include other visual signals that are not associated with commanded movements and that are not visual cue signals. As discussed in more detail below, a given assessment may include a plurality of visual tests.

As used herein, a "visual target signal" or "target signal," is a visual signal (e.g., a symbol, cue, text or other type of visual signal) that is associated with a commanded eye movement and/or a commanded body part movement. In some embodiments, the visual target signal alone conveys the commanded eye movement and/or body part movement. In other embodiments, the test subject is provided additional information in conjunction with the visual target signal (e.g., before or during display of the visual signal) that conveys the commanded eye movement and/or body part movement.

As used herein, a "visual cue signal" or "cue signal," is a visual signal (e.g., a symbol, cue, text or other type of visual signal) that is associated with a subsequent (e.g., upcoming) visual target signal. As illustrated below, a visual cue signal may provide information about the timing or location of the subsequent (e.g., upcoming) visual target signal and/or may provide information about the commanded movement associated with the upcoming visual target signal, In some embodiments, a visual cue signal provides a cue for a subsequent visual target signal, to help the subject prepare for the subsequent visual target signal and respond appropriately with the commanded eye movement and commanded body part movement associated with the subsequent visual target signal. For example, a visual cue signal may comprise a directional cue indicating the relative direction of the subsequent visual target signal.

FIG. 1 illustrates how a series of visual signals may be displayed, as a visual test, to a human subject. In the illustrated method, a cross (102) is displayed to the subject, such as on a screen, such as on an electronic screen (101), and the subject is or has been instructed to look at the center of the cross. Subsequently, a visual signal is displayed, replacing the cross. Shown here is an arrow (103). In some embodiments, the subject is or has been instructed that the direction of the arrow is a cue for the next visual signal, e.g., the arrow may embody a directional cue for the subsequent visual signal. In some embodiments, the subject has not been instructed that the direction of the arrow is a cue for the next visual signal. Next, an arrow pointing to a circle (104) is displayed. In this example, the circle is located at the direction indicated by the previously displayed arrow (103). Accordingly, the previously displayed arrow provided a directional cue (e.g., it is a visual cue signal) for the subsequently displayed circle. In specific embodiments, the subject is or has been instructed to look at the circle and perform a body part movement (e.g., press a button or depress a pedal) as soon as a circle is displayed. (Thus, in this example, the circle is a visual target signal.) As discussed in more detail below, an assessment of more complex neurological and/or psychological functioning can be effected if the circle is located at a direction opposite to that indicated by the previously displayed arrow. In some embodiments, the subject is or has been so advised, while in other embodiments that subject has not been so advised. (This would be a "misdirectional" cue signal, as discussed below.)

In some embodiments, different visual signals are associated with different body part movements. For example, different visual signals could be associated with steering left or steering right; pressing a button or pressing a pedal; pressing with the right hand/foot or with the left hand/foot., etc.

In accordance with the displays depicted in FIG. 1, the invention includes detecting whether the subject moved the eyes towards the target signal immediately following the appearance of the target signal, and the eye movement response latency (e.g., the time difference between when the target signal was displayed and when the eyes focused on the target). The invention also includes detecting whether the subject made the correct body part movement after the target signal was displayed, and the body part movement response latency (e.g., the time difference between when the target signal was displayed and when the body part movement was performed). Additionally or alternatively, in some embodiments, the invention includes detecting the fixation of the subject's gaze on the target signal.

It should be understood that the invention includes various visual signals and correlated eye and body part movements, including various cue signals and various target signals. For example, different signals can be selected that will trigger different cognitive processes associated with different neural systems, such as cue signals that are nondirectional (i.e., not indicating a direction), directional (i.e., indicating the direction, e.g., horizontal, vertical, diagonal, of the upcoming target signal), or misdirectional (i.e., indicating an incorrect direction of the upcoming target signal), and cue signals that are associated with instructions to not respond (inhibition cue signals), or to respond with a specific or opposite movement depending on the cue signal. With regard to directional cue signals, for example, a directional cue signal may indicate that the subsequent target signal will appear at a horizontal direction (e.g., left or right) relative to the directional cue, in a vertical direction (e.g., above or below) relative to the directional cue, in a diagonal direction relative to the directional cue, or in a direction towards the perimeter or center of the screen relative to the directional cue. The invention also includes three-dimensional embodiments, where the target signal may appear anywhere along an X-Y-Z axis, and where the cue signals may include corresponding directional and/or misdirectional cues.

The invention also includes embodiments where the target signal moves, including embodiments where the target signal moves in any one or more directions in a plane (e.g., in an X-Y direction) or in any one or more directions in three-dimensional space (e.g., in an X-Y-Z direction. In accordance with such embodiments, the cue signals may include corresponding directional and/or misdirectional cues. Also in accordance with such embodiments, the correctness of the responsive eye movement may be assessed with regard to whether and how closely the subject's eye movements track the movement of the target signal.

Figure 2:
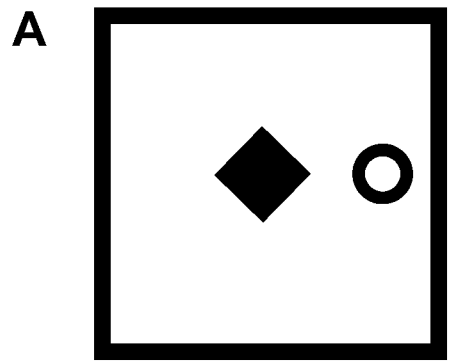
FIG. 2A-F illustrate different types of visual cue signals in a visual test, along with a visual target signal.
Figure 2:
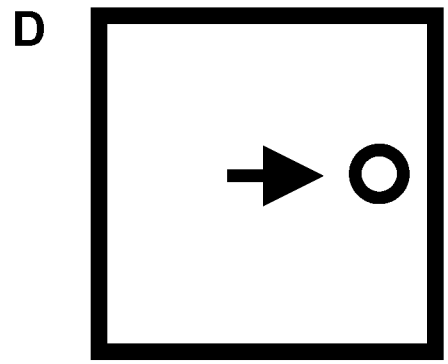
Figure 2:
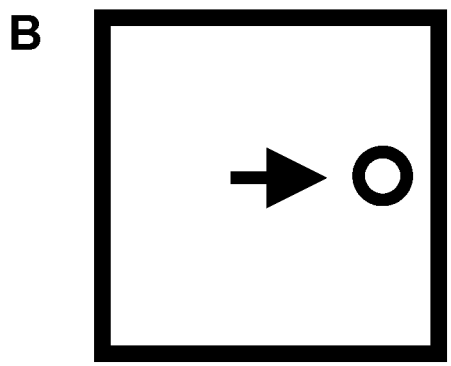
Figure 2:
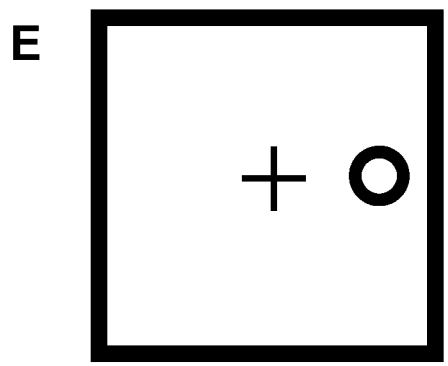
Figure 2:
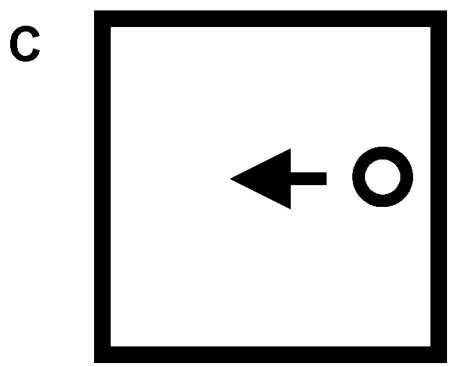
Figure 2:
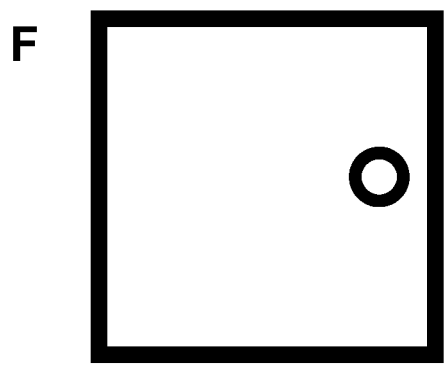

FIG. 2A-F illustrate various combinations of cue signals (left) and target signals (right). In FIG. 2A, the diamond may be a nondirectional cue signal, which may alert the subject that the target signal will be displayed soon. The arrow in FIG. 2B is similar to that in FIG. 1, and is a directional cue signal. The arrow in FIG. 2C points to the opposite direction from the target, and so is a misdirectional cue signal. In FIG. 2D, the arrow is colored or shaded, and the subject is or has been instructed not to follow the direction of the arrow (e.g., not to look at the target and/or not to respond with a body part movement). Thus, FIG. 2D illustrates an inhibition cue signal. In FIG. 2E, a cross is displayed initially and continues to be displayed when the target is displayed. Although the cross is not associated with any other information or instructions, its display may retain the subject's attention, and so it is referred to as an uncued fixation signal. In FIG. 2F, a cross is displayed initially and then is not displayed for a period before the target is displayed, resulting in an uncued gap signal. The following table illustrates how different cues can assess different neurological and psychological conditions and assess neurological and psychological status.

Types of Cues and their Indications

| FIG. | Type of Cue Signals | Expected Effect | Neurological Function |
|---|---|---|---|
| 2A | Nondirectional cue signal | Timing information | Alerting network |
| 2B | Directional cue signal | Directional information | Orienting network |
| 2C | Misdirectional cue signal | Distracting information | Executive network |
| 2D | Inhibition cue signal | Inhibiting information | Inhibition network |
| 2E | Uncued fixation cue signal | Fixation | Response speed |
| 2F | Uncued gap cue signal | Loss of fixation | Perceptual network |

For example, nondirectional and directional cue signals can assess a subject's alerting and orienting functions, respectively. Misdirectional cue signals provide erroneous or distracting information, and can assess the subject's ability to resist distraction which is correlated with the integrity of the subject's executive network. Inhibition cue signals assess the subject's ability to inhibit ocular and body part movements. Uncued fixation signals are useful for assessing reaction speed, while uncued gap signals are useful for assessing the subject's perceptual function. The forgoing illustrates the robust assessment and information that can be obtained using the systems, methods and devices described herein.

In some aspects, the invention involves displaying one or more visual signals to a human subject, comprising one or more target signals, wherein each target signal is associated with an intended eye movement and/or body part movement; detecting, following the display of each of visual signal, a responsive eye movement and/or body part movement, and assessing the neurological and/or psychological status of the subject based on, for example, the latency and/or correctness of the responsive eye and/or body part movements to the visual targets. In some aspects, the invention further comprises displaying one or more cue signals prior to the display of one or more target signals. As noted above, a cue signal can be a directional cue signal, a misdirectional cue signal, an inhibition cue signal, a fixation cue signal, or an uncued gap signal. In some aspects, the invention includes displaying a different cue signals prior to each of two or more target signals, including two or more different directional cue signals, a directional cue signal and a misdirectional cue signal, a directional cue signal and an inhibition cue signal, a directional cue signal and a fixation cue signal, a directional cue signal and an uncued gap signal, and any permutation and combination of any two or more cue signals, simultaneously and/or sequentially.

In some embodiments, one, more or all of the visual signals are displayed without a cue signal. In some embodiments, some visual signals are preceded by cue signals and some are not, either randomly or by design.

As noted above, the visual signals discussed herein are for the purpose of illustration only. Other types of signals and cues are included in the invention. For instance, a nondirectional cue signal can be of any shape, including a circle, a square, diamond, star, or irregular shape or symbol. A directional or misdirectional cue signal can be of any shape, including a line, arrow, triangle, arc, bracket, or irregular shape or symbol. An inhibition cue signal can be of any shape or can be provided as a symbol with a different color or shading than, for example, a corresponding directional cue signal, or can be provided as a flashing light or flashing signal. In some embodiments, words, pictures, and/or numbers can be used as visual signals. In some embodiments, the subject is instructed as to the meaning and (if applicable) intended response/commanded movement associated with one, some or all signals used in the assessment.

A.2 Modulation of Timing and Locations of Visual Signals

Visual attention can be influenced by the subject's expectations of when and where information of interest will be presented. In this context, it is noted that different brain systems are responsible for generating these expectations. Furthermore, attention is a cognitive processes that is vulnerable to impairment by many forms of neuropathology, including even mild brain injury, and also may be impacted by neurological and/or psychological status.

In some embodiments, the invention includes selecting and displaying visual signals in order to manipulate and modulate the subject's expectations about the timing and location of a subsequent visual signal, and assessing the subject's response when those expectations are met and/or are not met. These embodiments may be particularly useful for assessing a subject's visual attention and associated neurocognitive processes. For example, the use of directional and misdirectional cue signals can be used to manipulate and modulate the subject's location expectations and the use of nondirectional cue signals and uncued gap signals can be used to manipulate and modulate the subject's timing expectations, as discussed above. The subject's timing expectations also can be manipulated and modulated by the test parameters themselves, as discussed below.

Referring again to FIG. 1, each visual signal is displayed in a predetermined order with a selected time interval between displays. For instance, the cue signal (103) can be displayed for a brief moment (e.g., 200 ms) before the target signal (104) is displayed. Further, a rest interval can be provided between tests, e.g., between the display of each set of cue and target signals. A rest interval may be selected to provide sufficient time to allow the subject to reset and prepare for the next test, while not being so long that the subject becomes distracted or loses interest. In some embodiments, a visual signal is displayed during the rest interval, such as a cross-hairs signal.

In some aspects, a cue signal is displayed for about 200 ms before a target signal is displayed, or from about 50 ms to about 500 ms, including from about 100 ms to about 400 ms, and from about 150 ms to about 300 ms. In some aspects, each cue signal is displayed for about the same time interval before a target signal is displayed, such that the subject develops a timing expectation for the display of the target signal. In some aspects, one or more cue signals are displayed for a variable time interval, such that the target signal is displayed at an unexpected time relative to the display of the cue signal. In some aspects, the display duration of a cue signal is adjusted based on the subject's performance.

In some aspects, a target signal is displayed for about 200 ms, or from about 50 ms to about 500 ms, including from about 100 ms to about 400 ms, and from about 150 ms to about 300 ms. In some aspects, the display duration of a target signal is adjusted based on the subject's performance.

In some aspects, a rest interval is provided, lasting from about 50 ms to about 3500 ms, including from about 1500 ms to about 2500 ms In some aspects, each rest interval is provided for about the same time interval. In some aspects, one or more rest intervals is provided for a variable time interval. In some aspects, the duration of a rest signal is adjusted based on the subject's performance.

As noted above, the invention involves displaying one or more visual signals to a human subject, comprising one or more target signals, and, optionally, one or more cue signals associated with a target signal. The number of visual signals displayed to a given subject during a given assessment is not limited, but generally may range from the display of 10 to 1000 target signals, including 100, 150, 200, or 500 target signals. As noted above, a given assessment may include the display of different cue signals. Further, each cue signal may be displayed multiple times. Indeed, a given assessment may include the display of the same or different cue signals in a selected order or in a random order, or in an order that is partially selected and partially random. For example, an assessment may include a certain number of displays of a given cue signal (e.g., 10, 20, 30, 40 or 50 directional cues; 5, 10, 15, 20, or 25 inhibition cues; 10, 20, 30, 40, or 50 misdirectional cues, etc.) in a predetermined or random order, and/or may include a certain pattern of cue signals (e.g., fixation cue, followed by directional cue, followed by directional cue, followed by inhibition cue, followed by directional cue, followed by misdirectional cue, etc.). In some aspects, the cue signals are displayed in certain ratios, such that a given cue signal is displayed more or less frequently, or at the same frequency, as another given cue signal. While the display of more signals generally may result in a more robust assessment, the number of signals displayed in a given assessment may be limited by the subject's fatigue, boredom, etc. In some aspects, an assessment is completed within about 1 minute, about 5 minutes, about 10 minutes, about 15 minutes, about 20 minutes, about 30 minutes, about 45 minutes, or about one hour.

B. Methods of Detecting Responsive Movements

The invention is not limited to specific methods of detecting eye and body part movements. To the contrary, the present invention is not limited to any specific detecting and includes systems, methods and devices that achieve detection with systems, methods and devices known in the art.

In some embodiments, a sensor is used to detect the position of one or both eyes of a subject. A sensor can determine coordinate-based positions of the subject's gaze(s), which can be used to track eye movement, and determine whether eye movement occurred in the commanded direction and whether the subject has fixed his or her gaze on the target signal. A sensor also can assess the fixation of the subject's gaze, such as fixation on the target signal. Tracking movements of the eyes, pupils or gazes and assessing fixation can be readily carried out with conventional eye-tracking technologies.

In some embodiments, a subject's pupil's dilation and/or constriction also is detected. Such information can provide additional insight into a subject's neurological and/or psychological status and/or be useful for data analysis, such as being useful to indicate distraction, level of interest, fatigue, and/or effort.

Body part movements also can be detected with readily available technologies. For instance, the subject can be instructed to press a button, turn a steering wheel, move a joystick or depress a pedal. Non-limiting examples of buttons include a key on a computer keyboard, a button on a computer mouse, a button on a smart phone or tablet, or a virtual button displayed on a touch-sensitive screen.

B.1 Initiation of Assessment

Prior to initiation of a neuropsychological assessment, a human test subject can be given instructions on how the assessment is conducted. An exemplary instruction reads as follows.

Look at the cross in the center of the screen. When a target appears on the left, right, top, or bottom of the screen, look at it and press the button as quickly as possible. However, when you see a red arrow, don't look at the target or press the button.

(For these instructions, a red arrow would be an inhibition cue signal.)

To ensure test efficiency, the systems can be configured to ensure that the subject is ready and able to take the assessment. In some embodiments, before initiation of the assessment, the eye movements of the subject are monitored during a multimedia practice assessment, and this information is used to confirm that the subject is ready and understands the assessment procedure. For example, if incorrect eye movements are detected during the practice assessment, feedback can be provided to correct potential misunderstandings. If the practice assessment cannot be completed successfully, the assessment can be discontinued manually or automatically.

B.2 Testing, Adaptation and Recalibration

As discussed above, the display of different visual cue signals and the display of visual target signals at different locations and timings activate different cognitive and neural systems, such that differences in test performance in response to different visual tests can provide robust information as to the subject's neurological and/or psychological status. These design elements facilitate assessment of multiple identifiable cognitive processes and neural systems within a single, cohesive assessment that is more engaging for the test subject, and that can be completed in a short period of time (e.g., 1-15 minutes).

Further, the presence of different cue signals in each visual test facilitates measurements that are sufficiently reliable to be interpreted on an individual basis. That is, it does not require the comparison between one group of individuals to another group.

The process vastly improves the reliability of measurement and allows effective measurement with or without a head restraint or goggles to allow a more comfortable, user-friendly experience for patients/participants.

In some embodiments, the present technology can automatically respond adaptively in real time to address issues that may impact data validity. For example, in some embodiments, if a pre-defined number of invalid responses (e.g., eye or body part movements inconsistent with the instructions indicated on the visual test) occur during an assessment including a plurality of tests, the assessment may "pause" to identify and resolve the problem before resuming the assessment. For instance, if multiple "data loss" trials are encountered, the assessment may re-calibrate to re-establish data lock to the eye.

In another example, if multiple "unprepared" or "distracted" trials are encountered, the assessment may provide additional direction to the subject and verify that the subject is ready before proceeding. Also, if multiple "excessive movement" trials are encountered, the assessment may provide a warning about excessive movement before proceeding.

Additionally or alternatively, system recalibration can be included to retain efficiency of the technology. Software can be used in situations where calibration of gaze relative to the environment is not perfectly fixed (e.g., due to changes in head position with a remote eye tracker). In some embodiments, locations of the visual tests (relative to gaze position) can be estimated using periodic calibration trials where a subject is instructed to fixate upon the visual tests.

When appropriate, locations of visual tests (relative to gaze position) can be adjusted dynamically using data from a series of fixations. For example, the location for a target signal in one location can be determined using a rolling mean of the most recent number X (such as, for example, 6) of fixations so that target signals that are within the overall bounds are considered an acceptable fixation of that visual test.

Such recalibration enables the system to automatically account for "drift" in calibration over time. In some embodiments, the amount of "drift" can also be provided as a validity score.

C. Data Collection and Interpretation

D.1 Measured Parameters for the Eye and Body Part Movements

The present technology detects and measures certain characteristics of eye and/or body part movements responsive to visual tests.

In some embodiments, a "visual reaction time" (Visual RT), which measures the eye movement latency, is calculated as the time between the onset of display of the target signal (e.g., the circles on the right hand side in FIG. 2) and the beginning of a fixation of the eyes on the target signal. This process can be distinguished from other forms of "Saccadic reaction time (RT)" which are calculated as the time between the onset of display of the target signal and the beginning of a saccade toward the target signal.

It is contemplated that the Visual RT metric allows more robust and reliable measurement than a traditional Saccadic RT. The Visual RT metric is a performance indicator, in that completion of a fixation on a target represents a more complete task (e.g., target acquisition). Therefore, the Visual RT metric is also more closely linked to real-world functional abilities of interest to the test subjects.

Of course, the technology also includes aspects when Saccadic RTs (i.e., time to initiate the saccade) is calculated. All metrics based on Visual RT can be recalculated on the basis of Saccadic RT to eliminate time related to "eye travel" to the target.

In some embodiments, a "Visual RT consistency" is calculated, measuring the derivation, error, or confidence regions of the Visual RTs. Therefore, the Visual RTs reflect the consistency of the eye movements. In some embodiments, the Visual RT consistency is measured as the standard deviation or standard error of a group of Visual RTs (e.g., by test block or for the entire test). In some embodiments, performance errors are quantified by frequency of occurrence (ratio) relative to the total number of possible errors.

In some embodiments, a "Visual Omission error" is determined, which can be the occasion in which a subject's eye fails to fixate upon a target signal.

A "Visual Inhibition error," determined in some embodiments, can refer to the occasions in which a subject's eye fixates on a non-target signal. In some embodiments, a "stop-signal reaction time" is measured, as the amount of time needed for a user to receive a "stop" signal in order to effectively inhibit an inappropriate fixation. Additionally or alternatively, in some embodiments, a "Partial Visual inhibition error" is recorded when a user makes an eye movement toward, but not directly upon a non-target signal.

Additionally or alternatively, in some embodiments, an "overshoot error" is measured, when a subject makes an eye movement that goes past the target signal, and/or an "undershoot error" is measured when a subject makes an eye movement toward the target that does not reach the target signal.

In some embodiments, performance is determined dynamically, as the assessment is in progress, allowing for adaptive testing approaches whereby the test is modified on-the-fly to meet the test-taker at their ability level. For instance, the assessment can be lengthened or shortened in order to obtain sufficient data to achieve reliable scores. Another example is that the amount of time a visual signal is displayed is varied to modify test difficulty on-the-fly.

In some embodiments, when a visual signal is displayed to a subject, the system measures and records the performance of the subject in terms of body part response. In some embodiments, a "Manual reaction time (RT)" is calculated to indicate the body part movement latency, as the time between the onset of display of the target signal and an appropriate responsive body part movement (e.g., press of the correct button, correct movement of the joystick or steering wheel).

In some embodiments, also measured is a Manual RT consistency, which can be the standard deviation or standard error of the Manual RTs, serving as an indicator of consistency (variability) of the body part movement performance.

In some aspects, performance errors can be quantified by frequency of occurrence (ratio) relative to the total number of possible errors.

As discussed above for visual response measurements, various manual movement errors can be measured, including "Manual Omission errors" (in which a user fails to provide an appropriate responsive body part movement to a target), "Manual Inhibition errors" (in which a user provides a body part movement inappropriately, e.g., for a non-target), as can other parameters such as "Stop-signal reaction time" (the amount of time necessary for a user to receive a "stop" signal in order to effectively inhibit an inappropriate body part movement). Also, performance of the body part movement can be determined dynamically, as the assessment is in progress, allowing for adaptive testing approaches whereby the assessment can be modified on-the-fly to meet the test-taker at their ability level.

D.2 Error Detection

The present methods and systems can be configured to automatically identify individual data points from a given neuropsychological assessment, that are determined to be invalid and respond appropriately.

Types of invalid data points can include, without limitation, (A) lost data, e.g., visual tests where data loss (e.g., due to blinks or sensor problems) exceeds pre-defined thresholds; (B) unprepared subject, e.g., visual tests where the user's point of fixation was not centered when the target appeared; (C) distracted subject, e.g., visual tests where a subject's first fixation after the target appeared was somewhere other than the target signal itself (this may overlap with various error types described elsewhere); and (D) excessive movement, e.g., the subject moves the head beyond a threshold acceptable level of adequate data collection.

In some embodiments, once an invalid data point is detected, the invalid data point is screened from interpreted/scored data. In some embodiments, eye tracking-based validity indicators can be used to enhance the validity of both eye and body part movement data by screening data that may be invalid. In this respect, the resulting screened body part movement data are further cleaned up and improved, and thus can be considered "eye tracking-enhanced."

The present technology further provides methods and related software to evaluate invalid data points to aid interpretation of assessment performance. For instance, each data point can be accompanied with a validity indicator indicating validity on a continuous basis. Also, each assessment can have an indicator identifying quantity of data samples that are invalid from that assessment. This allows customizable decision rules with regard to how much lost data (or otherwise invalid data) is permissible to consider the assessment valid or invalid.

In some embodiments, after determination of the validity of each data point based on customizable rules described above, each of the invalid data points (including lost data, unprepared, and distracted forms of invalidity described above) are summarized as "validity scores". In this respect, cutoff values for each validity score can be used to determine (i) which scores to include in hierarchically-higher scores (e.g., which test scores to include in calculations of a composite subscale; which subscale scores to include in calculation of a composite scale score) and (ii) when the overall data set for a given test administration should be considered "invalid" or "questionable" in quality.

In some embodiments, the validity scores can be compared to a normative database, resulting in a standardized score representing the level of validity compared to a specified population. Such populations can include demographic, occupational, functional, clinical, effort, and validity characteristics to facilitate interpretation of results as valid/invalid and similar/dissimilar to populations of interest.

D.3 Test-Taking Efforts

The present technology also permits the consideration of the test subject's "test-taking effort." Test-taking effort can be helpful in determining whether the subject's responses reflect an accurate representation of true neurological or psychological status.

In some embodiments, score distributions are processed using an algorithm that compares performance to known performance profiles of "best effort" vs. "simulated poor performance." Poor effort can be characterized, for example, by distinct subgroups of normal and extremely slow visual reaction times (or long eye movement latency), substantially poorer body part movement performance than eye movement performance, slower than normal inhibition errors, and an error ratio that is unusually high in comparison to visual reaction time, or other factors.

D.4 Data Integration, Recordation and Output

The present technology also can include programs or software that aggregates, standardizes, and interprets visual and body part movement performance results for an individual subject.

In some embodiments, similar data types are aggregated using measures of central tendency (e.g., median visual RT for a given trial type; square root reciprocal for a trial type) and consistency (e.g., standard deviation of visual RT for a given trial type), based upon consideration of valid vs. invalid data points. Standard error is calculated for each metric of central tendency to provide a confidence interval for interpretation.

In some aspects, "trend" metrics are calculated representing linear or non-linear trends in primary variables over the course of the test (e.g., Visual RT trend: faster/slower RT over time; Visual Inhibition error trend: more or less errors over time). These metrics can be used to interpret increasing fatigue, task habituation, and other characteristics of the patient/user.

In some aspects, metrics representing visual vs. body part movement performance can be compared, resulting in relative metrics that are relevant to neural function and task validity (e.g., relative visual vs. manual RT).

Metrics representing performance under various conditions (e.g., following various cue types; following various stimulus latencies; for left vs. right targets; for horizontal vs. vertical targets) can be compared to derive scores that are relevant to neurological and/or psychological status. Metrics representing performance are compared to a normative database, resulting in a standardized score representing the level of performance compared to a specified population. For instance, normal/healthy peers, or peers subject to a specified condition or state of interest (e.g., traumatic brain injury; high levels of fatigue; high levels of depression; poor task effort).

In some aspects, metrics representing an individual's performance can be compared to the individual's own previous performance on the same assessment to identify changes in performance over time. Statistical analyses can be automatically applied to determine whether a given set of results are significantly different from individual or aggregate other test taking occasions. This can be used to track improvement or decline in performance including changes relevant to development, training, medical care, or progression of a clinical condition.

Metrics representing an individual's performance can also be compared to the individual's own previous performance on other assessments to identify inconsistencies in performance between assessments. Statistical analyses can be applied to determine whether a given set or results are significantly different from individual or aggregate other results. This can be used to derive significant strengths and weaknesses. Profiles of multiple performance variables are compared to normative databases, resulting in a standardized score representing the degree of similarity of an individual to a specified population.

The technology (e.g., software) also can be configured to automatically provide numerical, graphical and textual output to aid interpretation of results. For example, numerical output can be provided at the level of the individual data points and summary/composite test metrics described elsewhere. Graphical output can be provided comparing summary test metrics from the individual to specified populations within a normative database. Narrative reports can be generated describing the clinical or operational significance of test metrics in relation to specified populations within a normative database. Differing levels of detail can be provided based upon the purpose of the assessment or qualifications of the examiner/health care provider (e.g., screening report vs. extended report). Of course, these examples are not limiting.

The technology (e.g., software) also can be configured to automatically and securely store raw, processed, and aggregated data and results in a database for future retrieval. In some embodiments, the technology can transfer raw, processed, and aggregated data to remote servers (including in an encrypted/secure fashion, consistent with HIPAA and other regulatory guidelines as appropriate) to permit additional storage, processing, and analysis by examiners (e.g., trained professionals) who may not be present where the data was collected. This allows for a "telemedicine" approach (for medical applications) or "tele-interpretation" approach (for non-medical applications) and facilitates use of the technology in environments where highly trained personnel may not be available.

D. Clinical Uses and Advantages

The present technology can be used for various neuropsychological assessments for both healthy individuals and those diagnosed with or at risk of developing neurological and/or psychological conditions or disorders. Non-limiting examples of conditions and disorders include concussion, brain injury, ADHD, dementia, HIV-associated neurocognitive disorders, stroke, Parkinson's disease, multiple sclerosis, brain tumor, hypoxia, hydrocephalus, seizure disorder, brain infection, Huntington's Disease, learning disabilities, cerebrovascular disease, toxic exposure, depression, anxiety, post-traumatic stress, and traumatic brain injury.

Compared to conventional eye-tracking methods, the present technology has shown multiple advantages, as evidenced in the Examples. In summary, the successes include:

- It reliably elicits neurocognitive processes of interest (alerting, orienting, gap, and executive/interference effects);
- It is sensitive to traumatic brain injury (TBI);
- It can detect "traditional" cognitive domains of Attention, Executive Function, and Psychomotor Speed;
- It is resistant to the effects of confounds such as depression, traumatic stress, combat exposure, and fatigue; and
- It can be completed in 15 minutes vs. 2 hours for a comparable cognitive battery.

E. Validating Performance

Also described herein are methods for validating a subject's performance on a visual test. Such methods may comprise displaying a visual test to a subject wherein the visual test is associated with a visual or body part response, detecting an eye movement and, optionally, a body part movement, and assessing performance validity based on one or more of a responsive movement, a non-responsive movement, and an involuntary movement.

The visual test can be any visual test, including but not limited to the visual tests described above. For example, regardless of the performance task of the test, the method or system can monitor eye movements to assess validity of the subject's performance, such as to determine whether individual trials of the test are valid (e.g., did the subject look away for a moment), or to determine if the test as a whole is valid (e.g., was the subject malingering or sandbagging). In this respect, Example 5 illustrates the use of this methodology to assess performance validity with high levels of specificity and sensitivity. Such validation can be used in place of, or as a supplement to, the lengthy and cumbersome standalone tests that are commonly used to assess performance and symptom validity in conventional neuropsychological assessments. For example, the validation method or system could be used in connection with other known tests, such as the ANAM or ImPACT tests. Moreover, the use of this validation method could be used to develop a knowledge database of specific patterns of eye movements that are associated with common performance levels, such as malingering versus "best efforts."

The visual or body part response can be any visual or body part response, including any visual or body part response discussed above, or a different visual or body part response, including providing a response to a question or comment embodied in the visual test, such as by marking, writing, or stating a response (e.g., answering a question). The detected eye movements can be one or more of voluntary eye movements, involuntary eye movements, responsive eye movements and non-responsive eye movements. The detected body part movements can be one or more of voluntary body part movements, involuntary body part movements, responsive body part movements and non-responsive body part movements. Additionally or alternatively, the method may comprise detecting pupil dilation.

Poor performance validity may be indicated by one or more of a lack of response (e.g., a lack of a responsive eye and/or body part movement), an incorrect response, a response with an abnormal latency, a response lacking coordination between the eye and body part movements, or an abnormally high frequency of any one or more of the above in a series of tests (e.g., in an assessment). Additionally or alternatively, poor performance validity may be indicated by one or more non-responsive movements, such as if the subject's eye movements reveal that the subject was not monitoring the stimulus (e.g., was not gazing at the crosshairs during a rest period). Additionally or alternatively, poor performance validity may be indicated by involuntary movements, such as pupil dilation, eye blinks, etc.

In some embodiments, the method comprises comparing the subject's performance to a normative database. Additionally or alternatively, in some embodiments, the method comprises comparing the subject's performance to the subject's previous performance.

F. Computer Systems and Networks

The methods described here, in whole or in part, can be implemented on a computer system or network. For instance, instructions for displaying a visual test can be stored in a non-transitory computer-readable medium. Execution of such instructions can be carried out by a computer system, networked or standalone. Display of a visual test, in some embodiments, can be on an electronic screen that is connected, locally or remotely, to the computer system. A suitable computer system can include at least a processor and memory; optionally, a computer-readable medium that stores computer code for execution by the processor. Once the code is executed, the computer system carries out the described methodology.

In this regard, a "processor" is an electronic circuit that can execute computer programs. Suitable processors are exemplified by but are not limited to central processing units, microprocessors, graphics processing units, physics processing units, digital signal processors, network processors, front end processors, coprocessors, data processors and audio processors. The term "memory" connotes an electrical device that stores data for retrieval. In some embodiments, therefore, a suitable memory is a computer unit that preserves data and assists computation. More generally, suitable methods and devices for providing the requisite network data transmission are known.

Also contemplated is a non-transitory computer readable medium that includes executable code for carrying out the described methodology. In certain embodiments, the medium further contains data or databases needed for such methodology.

Embodiments can include program products comprising non-transitory machine-readable storage media for carrying or having machine-executable instructions or data structures stored thereon. Such machine-readable media may be any available media that may be accessed by a general purpose or special purpose computer or other machine with a processor. By way of example, such machine-readable storage media may comprise RAM, ROM, EPROM, EEPROM, CD-ROM or other optical disk storage, magnetic disk storage or other magnetic storage devices, or any other medium which may be used to store desired program code in the form of machine-executable instructions or data structures and which may be accessed by a general purpose or special purpose computer or other machine with a processor. Combinations of the above also come within the scope of "machine-readable media." Machine-executable instructions comprise, for example, instructions and data that cause a general purpose computer, special-purpose computer or special-purpose processing machine(s) to perform a certain function or group of functions.

EXAMPLES

Throughout the examples, an eye movement is also referred as an oculomotor response, a visual response, or a saccadic response, and a body part movement is referred to as a manual response, and a visual test, which includes a target signal and optionally a cue signal, also is referred to as a trial. Various measurements of visual and manual responses (e.g., visual reaction time and manual reaction time) reflect the latency and correctness of the eye and body part movements. Various cues and target signals are used as non-limiting examples of visual cue and target signals.

Example 1

An Exemplary Workflow for Neurocognitive Assessment

A system and procedure, referred to as Bethesda Eye Attention Measure (BEAM), was designed to evaluate multiple components of attention and executive functions of a test human subject. Primary variables collected included oculomotor responses (i.e., latency and/or correctness of eye movements, including fixation latency and fixation errors) and manual motor responses (i.e., latency and/or correctness of body part movements, including button press latency and button press errors). Individual cognitive processes were measured parametrically by systematically varying task characteristics across multiple trials. Trial types were intermixed and "littered" to eliminate predictability and enhance subject engagement in the task.

A. Pretesting Procedure

Setup: Participants were seated with their head unrestrained approximately 24" from and level with the center of the computer display and head/eye sensors. The eye sensor was directed toward the participant's right eye. The eye tracker was calibrated using a nine-point display. The calibration process takes approximately 2 minutes to complete. Eye and head movement data collection was then initiated at 120 Hz with event markers synchronized to the presentation of stimuli and manual motor responses.

Instructions: Prior to the testing, each person was given the following instruction: "Look at the cross in the center of the screen. When a target appears on the left, right, top, or bottom of the screen, look at it and press the button as quickly as possible. However, when you see a red arrow, don't look at the target or press the button."

B. Cognitive Processes Measurements

The primary measurements for eye movements included visual reaction time (saccadic RT), the latency in ms from the appearance of a target until the subject fixates on the target signal. The primary measurements for body part movement included manual reaction time (manual RT), the latency in ms from the appearance of a target signal until the subject pressed the button. Consistency of saccadic and manual RT (variability) were also considered primary measurements. Other measurements included: saccadic omission errors, in which the subject fails to fixate on a correct target signal; saccadic commission errors, in which the subject fixates on an incorrect target signal; manual omission errors, in which the subject fails to press the button for a correct target signal; manual commission errors, in which the subject presses the button for an incorrect target signal. With these measured parameters, the assessment was used to determine various cognitive processes as listed in Table 1.

TABLE 1

Types of Measured Neurocognitive Processes

Speed (central tendency)

Definition: How quickly can the subject detect a target and respond?
Example metric: Saccadic and manual RT on uncued trials
Consistency (variability)

Definition: How consistent is the speed of the psychomotor response?
Example metrics: Standard Deviation (primary) and Intra-individual coefficient of variation (ICV; secondary) for Saccadic and manual RT
Note: Consistent with RT variability literature in aging, HIV/AIDS, etc. Believed to reflect general biological properties (e.g., white matter integrity) of the motor systems.
Alerting Definition: What is the RT benefit of knowing when a target is about to appear?
Example metric #1: Saccadic and manual RT on nondirectionally-cued trials
Note: This "alerting" process is modulated by noradrenergic activity (Marrocco, Witte, & Davidson, 1994; Posner, 2008; Posner & Rothbart, 2007), and has been associated with neural activity in the right frontal cortex, the parietal cortex, and the locus coeruleus (Fan, McCandliss, Fossella, Flombaum, & Posner, 2005).
Example metric #2: Saccadic and manual omission errors. This metric reflects more basic vigilance processes.
Perceptual Shifting Definition: What is the RT cost of having to disengage from an existing stimulus before they can re-engage a new one?
Example metric: Saccadic and manual RT on "Gap" trials
Note: The presence of overlapping stimuli places additional demands upon systems responsible for visual disengagement, resulting in slower responses to the new stimulus (Fischer & Breitmeyer, 1987; Weber & Fischer, 1995). This process appears to be related to the functioning of the posterior parietal lobes (Posner & Cohen, 1984).

TABLE 1-continued

Types of Measured Neurocognitive Processes

Predictive Orienting

Definition: What is the RT benefit of knowing where a target is about to appear?
Example metric: Saccadic and manual RT on directionally-cued trials
Note: Predictive orienting processes appear to be modulated by acetylcholine (Davidson & Marrocco, 2000; Posner, 2008; Posner & Rothbart, 2007), with associated neural activity in the superior parietal cortex, temporal parietal junction, frontal eye fields, and superior colliculus (Corbetta & Shulman, 2002).

Interference Orienting

Definition: What is the RT cost of receiving inaccurate information?
Example metric #1: Saccadic and manual RT on misdirectionally-cued trials
Example metric #2: Number of fixation errors in the direction of the misdirectional cue
Note: These processes are related to activity in the right ventral frontoparietal network, including ventral frontal cortex, temporoparietal junction, frontal eye fields, and anterior cingulate cortex (Corbetta & Shulman, 2002).

Inhibition

Definition: How well can the subject inhibit a prepotent response?
Example metric: Number of saccadic and manual commission errors on "STOP" cue trials
Note: This is an eye tracking implementation of a Go/No-Go task. This process reflects function of frontal eye fields (saccadic commissions only) as well as right inferior prefrontal cortex, basal ganglia, and anterior cingulate cortex.

Ocular-Manual Quotient

Definition: What is the relative speed of Saccadic versus Manual RT?
Example metric: manual RT divided by saccadic RT
Note: Saccadic RT is much faster than manual RT in most healthy individuals. A reduced advantage of saccadic over manual RT may be related to neurocognitive impairment or neural injury.

Performance Validity

Definition: To what degree do the results represent the best possible performance of the subject? To what degree are the results of the testing interpretable within the context of a neurodiagnostic, neurocognitive, or neuropsychological assessment?
Example metrics: Certain numbers and types of valid versus invalid trials and other patterns of performance that are highly unusual among subjects providing their best possible performance. These metrics are determined empirically as described in the example below.
Note: An example metric used to determine performance validity is RT variability. Whereas RT variability metrics may provide neurodiagnostic, neurocognitive, or neuropsychological predictive value when performance is within a certain range, extremely high variability, beyond the range associated with genuine impairment, may provide a strong indication that the overall testing results are invalid.

Engagement

Definition: How much does the pupil respond when a target appears?
Example metric: Pupil width during target fixation divided by pupil width during cross fixation
Note: Pupillary response has been related to interest, cognitive load, fatigue, etc. This application is an exploratory index of task validity.

Data were automatically screened to exclude data for potentially invalid trials when the subject was not looking at the center of the display immediately before the cue/target signals appeared, or when there was a blink or missing eye data during the target signal presentation. Additionally, the saccadic RT value or saccadic commission value for a trial is considered invalid if, when the target appears, the subject looks away from the central fixation at a non-target location before looking at the target. Invalid values determined by these and related methods are excluded from primary scoring to prevent undesired influence of invalid scores upon analysis and interpretation of the test.

C. Trial Types

The following cues (cue signals) were included in the visual tests displayed to the test subjects:

Uncued Gap (UCG)
  Blank (empty) cue
Uncued Overlap (UCO)
  No cue (fixation cross remains)
Nondirectional Cue (NDC)
  White diamond
Directional Cue-White (DCW)
  White arrow (pointing toward the target location)
Directional Cue-Red (DCR)
  Red arrow (pointing toward the target location—"NO-GO")
Misdirectional Cue (MDC)
  White arrow (pointing opposite the target location)

Various timelines, concerning the sequence and interval periods, were used during the visual tests. All of the times, however, included all of the above-listed trial types (e.g., all of the above pairs of visual cue signals and target signals).

D. Cue Compositions

Different trial types were mixed within each subtest in a counterbalanced, pseudorandom way. Table 2 below illustrates some representative test sets.

TABLE 2

Trials in Representative Test Sets

| SUBTEST | TRIAL TYPE | | | | | | TOTAL TRIALS PER BLOCK |
| --- | --- | --- | --- | --- | --- | --- | --- |
| | UCG | UCO | NDC | DCW | DCR | MDC | |
| Practice | 4 | 4 | 4 | 4 | 4 | 4 | 24 |
| Block 1 | 8 | 8 | 8 | 8 | 8 | 8 | 48 |
| Block 2 | 8 | 8 | 8 | 8 | 8 | 8 | 48 |
| Block 3 | 8 | 8 | 8 | 8 | 8 | 8 | 48 |
| Block 4 | 8 | 8 | 8 | 8 | 8 | 8 | 48 |
| Total | 36 | 36 | 36 | 36 | 36 | 36 | 216 |

Figure 3:
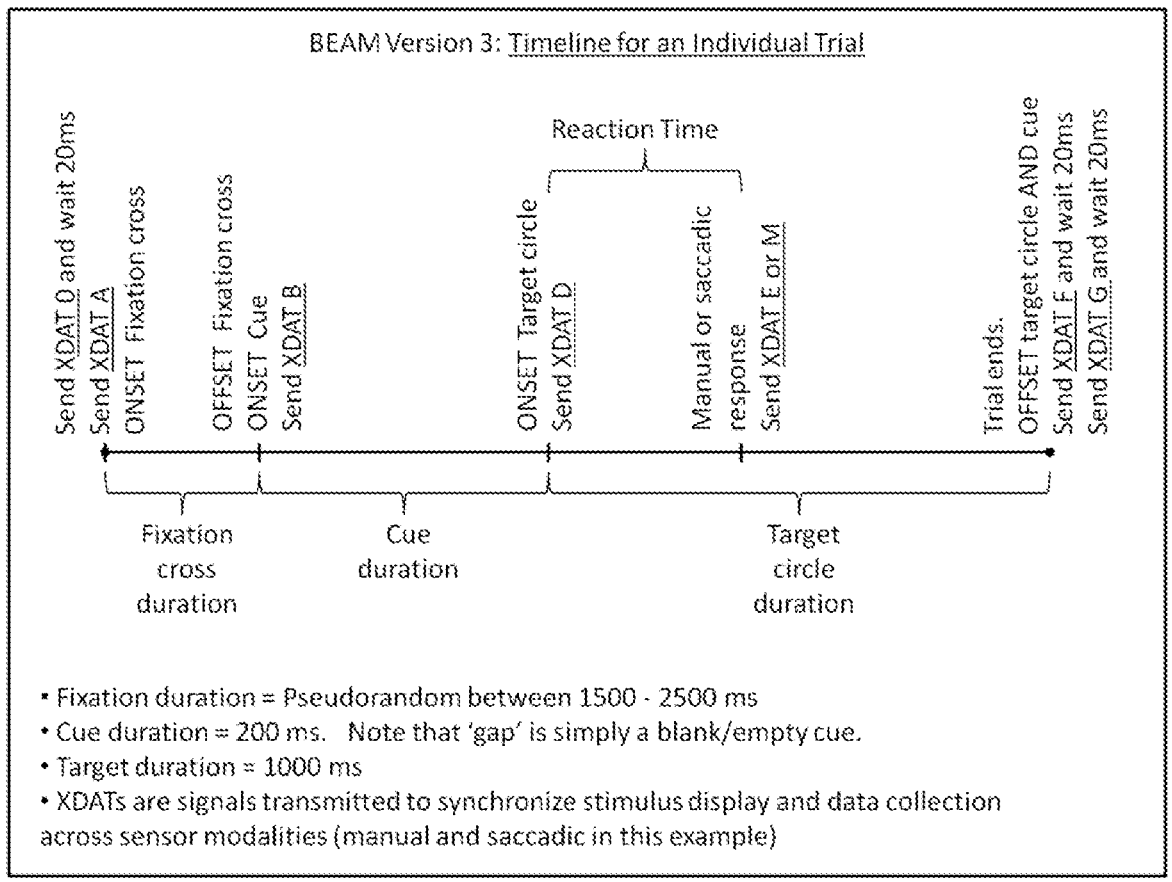
FIG. 3 presents an example timeline for displaying different visual tests during a neuropsychological assessment.

Total subtest time (practice+4 blocks) was about 10 minutes (see FIG. 3).

When selecting trial types, the following criteria were considered:
1. Trial types were presented in multiples of 4 to allow for an equal counterbalancing of target directions in Blocks 1-4;
2. All cue types were distributed evenly across blocks to ward off potential effects related to cue distribution;
3. Instead of a 5 (cues)×2 (gaps)×2 (go/no-go) framework (with 20 cells total), selected trial types were compared directly in a 6-cell design to make data collection more efficient and prevent the confounding of main effects by potential interactions; and/or
4. Red "stop" cues were directional (arrows) and oriented toward the target location in order to maximize the difficulty of inhibiting the pre-potent response.

Sensors used in the prototype included eye movement sensors (optics focused on the eye), head movement sensors (optics focused on the head), and body movement sensors (a button to be pressed). An ASL High-Speed D6 remote eye tracker recorded eye and head movements. The prototype sensors could be replaced by a variety of other sensors providing data relevant to movement of eye, pupil, or body, with minimal or no changes to the core technology system or method. Additional sensors were added as inputs to the digitizer to integrate supplementary sensors (e.g., EEG, fMRI, MEG, fNIRS, TCD, heart rate or pulse sensor, etc) into the data stream for correlation with eye, pupil, and body movements during performance of the test.

The assessment procedure described here can be used to assess additional cognitive processes, such as learning, memory, and working memory through the use of modified stimuli and methods. For instance, visual or auditory stimuli can be repeatedly paired with a specific target location. Shape A could be presented immediately before the appearance of "left" targets, whereas shape B could be presented before "right" targets. Individuals with intact memory should show reduced latency of response over time as they learn the pairings between cues and target locations. Similar metrics as used elsewhere (e.g., RT) could then be used as an index of learning. Supplementary memory indices are also drawn from the learning slope (slope of RT across exposure trials) and errors. Delayed recall trials (similar trials after a 10 or 20 minute delay) can be used to assess recall.

In another example, subjects can be instructed to remember target locations across a series of trials. Next, the pattern of target locations is repeated. Subjects with memory for the pattern of target locations will demonstrate reduced latency in response to those targets.

E. Data Processing and Scoring.

Custom software determined saccadic and manual reaction times (saccadic RT and manual RT) for each trial type. This system automatically extracts performance from the portions of each trial that are relevant to the cognitive process of interest, automatically filtering out responses that fall outside of the very closely-monitored conditions of valid performance. Block change of each variable is also computer to permit identification of changes in performance over time during the course of the test (i.e., reduced performance over time, across multiple trials).

Example 2

Validation of BEAM as a Reliable Measure of Neurocognitive Function

Methods: Example 1 provides a continuous performance test, referred to as BEAM, requiring oculomotor and manual responses to target stimuli across multiple test trials. Several unique trial types, each eliciting different aspects of cognitive processing, were presented pseudorandomly according to the configuration described in Table 2. Stimuli and procedures for this clinically-oriented task were designed to parametrically manipulate and measure speed, consistency, alerting, perceptual shifting, predictive orienting, interference orienting, and inhibition processes, along with Ocular-Manual Quotient, engagement, and performance validity. Internal reliability analyses were conducted using a data set with missing RT data (13.13% total) imputed using expectation maximization.

Participants: Participant characteristics for the sample of 54 Healthy Controls are summarized in Table 3.

TABLE 3

Participant Demographics - Healthy Controls

| | Control Group |
| --- | --- |
| N | 54 |
| Female | 53.70% |
| Mean age in years (SD) | 33.17 |
| | (11.42) |
| Mean years education (SD) | 16.20 |
| | (2.63) |
| Mean estimated premorbid IQ (SD) | 108.59 |
| | (11.23) |
| Race/Ethnicity | |
| White | 30 |
| Hispanic | 3 |
| Asian | 4 |
| Black | 15 |
| Other | 2 |

Figure 4:
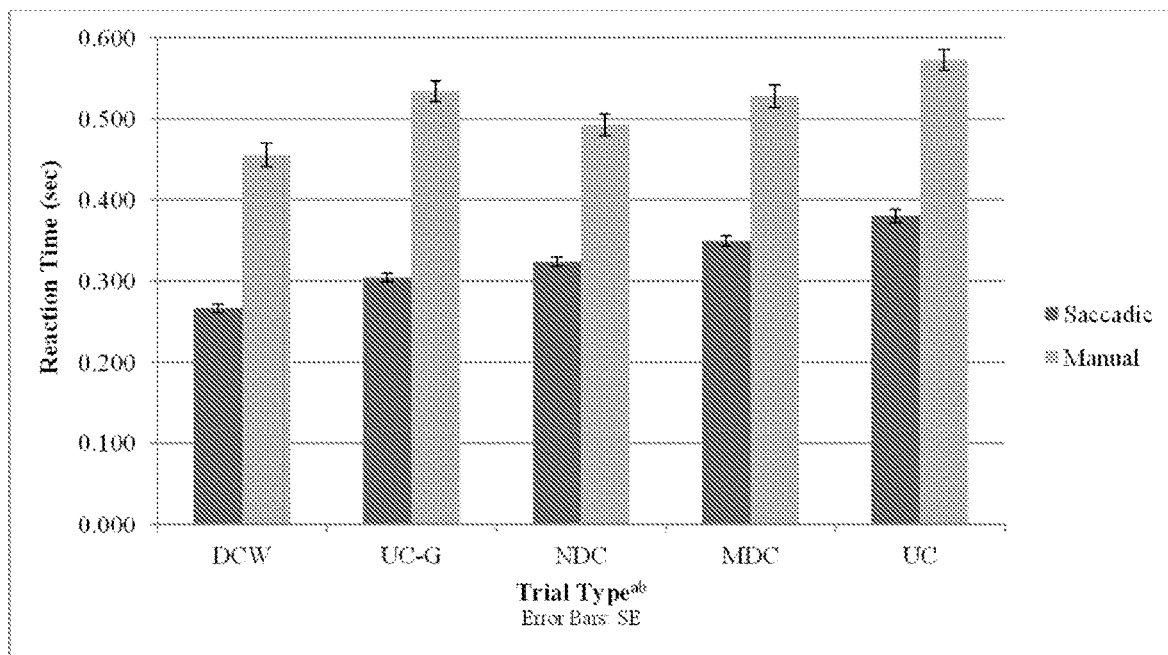
FIG. 4 presents the reaction time (saccadic and manual, respectively) for each type of cue type and response modality, as tested in Example 2.

Results—BEAM Reaction Times: The system was well tolerated by participants, and demonstrated excellent internal reliability for overall Saccadic RT ($\alpha=0.96$) and overall Manual RT ($\alpha=0.99$). Reliability for individual trial type RTs, as shown in Table 4, were good to excellent. Repeated measures ANOVAs indicated that Saccadic RT was significantly faster than Manual RT ($F[1,53]=207.95$, $p<0.001$, partial $\eta^2=0.80$). Additionally, there was a significant effect for cue type ($F[3.20,169.76]=162.96$, $p<0.001$, partial $\eta^2=0.76$), with all cue types (DCW vs. NDC, MDC, UCG, UC) significantly different from one another in post-hoc tests ($p<0.01$). The modality*cue interaction was also significant ($F[3.16,167.43]=18.697$, $p<0.001$, partial $\eta^2=0.26$), indicating that the effect of the cues differed by saccadic vs.

manual response modality. The results are summarized in FIG. 4, which shows the reaction time (saccadic and manual, respectively) for each type of cue. It can be seen that, for each type of cue, the reaction time is similar among test subjects, while the differences between cue types were much greater. Additionally, it can be seen that the manual responses took significantly (***p<0.001) longer time than the saccadic responses.

TABLE 4

Internal Reliability of BEAM Reaction Times among Healthy Controls

| Variable | Chronbach's Alpha |
|---|---|
| Saccadic RT (Overall) | 0.96 |
| DCW | 0.81 |
| NDC | 0.86 |
| MDC | 0.88 |
| UCG | 0.85 |
| UC | 0.87 |
| Manual RT (Overall) | 0.99 |
| DCW | 0.97 |
| NDC | 0.97 |
| MDC | 0.97 |
| UCG | 0.97 |
| UC | 0.97 |

Figure 5:
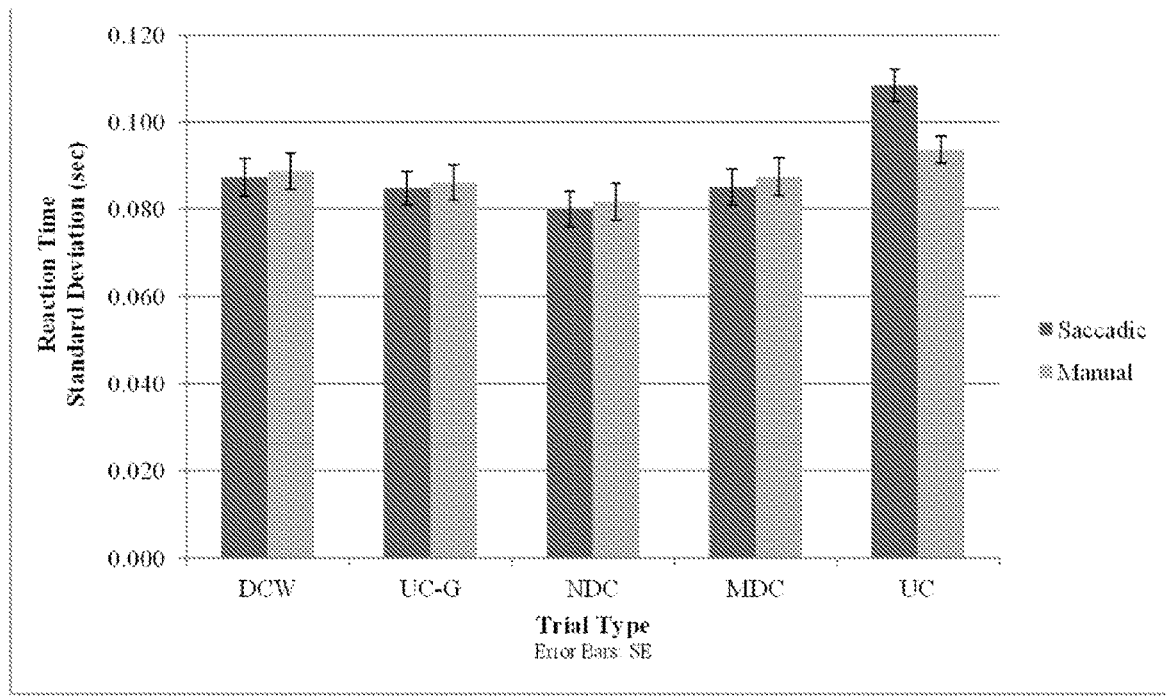
FIG. 5 shows the reaction time variability for each type of cue type and response modality, as tested in Example 2.

Results—BEAM Reaction Time Variability: Repeated measures ANOVAs indicated that RT variability was significantly influenced by cue type (F[4,212]=13.18, p<0.001, partial $\eta^2$=0.20). Post-hoc tests showed that RT variability for the UC cue was significantly greater than all other cues (p<0.05); and RT variability for the NDC cue was significantly less than all other cues (p<0.05) except for UCG. Saccadic RT was not significantly more variable (inconsistent) than Manual RT overall (F[1,53]=0.18, p=0.67, partial $\eta^2$=0.00). However, a significant modality*cue interaction F[4,212]=3.84, p<0.01, partial $\eta^2$=0.07) indicated that the effect of cue on variability also differed across modality. The results are summarized in FIG. 5, which shows the differences in reaction time variability (saccadic and manual, respectively) for each type of cue.

Results—BEAM Omission and Commission Errors: Dependent-samples t-tests indicated that commission errors were much more frequent within the saccadic modality (13.69% of valid trials; SD=13.14%) than within the manual modality (0.67% of valid trials; SD=2.02%; t(53)=7.41, p<0.001). However, frequency of omission errors did not differ significantly between the saccadic modality (0.79% of trials; SD=2.08%) and the manual modality (0.98% of trials; SD=2.48%; t(53)=−0.48,p=0.63).

Conclusions: These data demonstrate differences in performance by cue type, providing strong evidence that the system of the present disclosure can reliably measure and differentiate multiple neurocognitive processes. Additionally, the findings that the effects of cue type and frequencies of commission errors differ by saccadic vs. manual responses provide strong evidence that the combination of ocular and manual movement enables the system to measure neurocognitive characteristics that would be undetected using a single modality.

Example 3

BEAM Sensitivity to Presence and Number of Mild TBIs

Methods: A study was undertaken to evaluate the use of the invention to detect residual neurological impairment associated with mild TBI. The study followed the BEAM procedures as described in Examples 1 and 2. In addition to completing the BEAM, participants completed a 90-minute battery of conventional neuropsychological tests (see Table 5 for the full test battery). An additional group of participants with a history of mild Traumatic Brain Injury (TBI) were included in this study to supplement the group of healthy control participants; analyses were conducted on the combined sample of healthy controls and individuals with a history of mild TBI. Number of mild TBIs was truncated to a maximum of 5 to reduce the impact of outliers. In order to simplify interpretation of similar BEAM variables, a diagnostic algorithm was applied in which saccadic and manual median RT and variability for each trial type were determined to be "normal" (sample-standardized Z<1.0), "marginal" (sample-standardized Z>=1.0 but <2.0), or "impaired" (sample-standardized Z>=2.0) for each participant. "Normal" metrics were assigned 0 points, whereas "marginal" metrics were assigned 1 point and "impaired" metrics were assigned 2 points. By summing the individual metrics, the algorithm provided separate scores for "Saccadic RT Impairment" and "Manual RT Impairment" representing the number and severity of abnormal RT and variability scores within each response modality. Additional variables examined included the proportion of Saccadic and Manual Omission and Commission Errors, and the relative RT of overall manual vs. saccadic responses for each individual (the Ocular-Manual Quotient).

TABLE 5

Conventional Neuropsychological Test Battery by Domain. Neuropsychological Domains consisted of means of the following measures:

Global Cognition

Motor, Speed, Attention, Executive Function, and Memory Domains
Motor

Grooved Pegboard Dominant Hand (Reitan, *AMA Arch Neural Psychiatry* 73(1): 28-35, 1955)
Grooved Pegboard Nondominant Hand (Reitan, 1955)
Speed Trail Making Test Part A (Reitan, 1955)
CPT-II Hit RT (Conners, C. K., & MHS Staff (2000). Conners' CPT-II: Continuous performance test-II. Toronto, ON: Multi-Health System (MHS))
D-KEFS CWIT Trial 1 (Delis, Kaplan and Kramer, Delis-Kaplan Executive Function System (D-KEFS): Examiner's manual. San Antonio, TX: The Psychological Corporation; 2001)
D-KEFS CWIT Trial 2 (Delis, Kaplan and Kramer, 2001)
WAIS-IV Symbol Search (Wechsler (2008) WAIS-IV administration and scoring manual. San Antonio, TX: Pearson)
Attention WAIS-IV Digit Span Forward (Wechsler, 2008)
CPT-II Omissions (Conners, 2000)
Executive Functions WAIS-IV Digit Span Backwards (Wechsler, 2008)
CPT-II Commissions (Conners, 2000)
CPT-II Hit RT Standard Error (Conners, 2000)
Trail Making Test Part B (Reitan, 1955)
D-KEFS CWIT Trial 3 (Delis, Kaplan and Kramer, 2001)
D-KEFS CWIT Trial 4 (Delis, Kaplan and Kramer, 2001)

TABLE 5-continued

Conventional Neuropsychological Test Battery by Domain.
Neuropsychological Domains consisted of means of
the following measures:

Memory

CVLT-II Trial 1 -5 Total Delis, Kramer, Kaplan and Ober California
Verbal Learning Test (2nd ed.)Psychological Corporation, San
Antonio, TX (2000))
CVLT-II Short Delay Free Recall (Delis, Kramer, Kaplan and Ober,
2000)
CVLT-II Long Delay Free Recall (Delis, Kramer, Kaplan and Ober,
2000)

Results—History of Mild TBI: Demographics for the Mild TBI group are presented in Table 6. Mild TBI and Healthy Control groups did not differ significantly in age, education, gender, ethnicity, or estimated premorbid IQ. In a binary logistic regression model, greater Saccadic Impairment was significantly predictive of prior history of mild TBI (Wald=3.88, p<0.05). The odds ratio indicated that participants with high levels of Saccadic Impairment (i.e., Z>=1 in this sample) were 61% more likely to be in the Mild TBI group. A repeated measures ANOVA demonstrated a significant interaction of (TBI history*modality*cue), $F(3.28,259.46)=3.19$, p<0.05, partial $\eta^2=0.26$, indicating that the relationship between saccadic and manual responses across cue types (e.g., components of the Ocular-Manual Quotient) differed significantly between individuals with and without a history of TBI. Lower Ocular-Manual Quotient (indicating a reduced saccadic RT advantage over manual RT as compared to other participants in the sample) was also significantly predictive of prior history of mild TBI (Wald=4.43, p<0.05). The odds ratio indicated that participants with low Ocular-Manual Quotients (i.e., Z<=-1 in this sample) were 75% more likely to be in the Mild TBI group. Separate models predicting group membership from Manual Impairment score (Wald=0.24, p=0.62), Saccadic Commissions (Wald=0.78, p=0.38), Saccadic Omissions (Wald=0.35, p=0.56), and Manual Omissions (Wald=0.59, p=0.44) were non-significant. There was a non-significant trend for higher Manual Commissions to also be predictive of Mild TBI history (Wald=3.62, p=0.06).

TABLE 6

Participant Demographics - Mild TBI and Control Groups

|  | Control | Mild TBI | p[a] |
|---|---|---|---|
| N | 54 | 27 |  |
| Female | 53.70% | 59.26% | .635 |
| Mean age in years (SD) | 33.17 | 34.93 | .529 |
|  | (11.42) | (12.59) |  |
| Mean years education (SD) | 16.20 | 16.04 | .777 |
|  | (2.63) | (2.16) |  |
| Mean estimated premorbid IQ (SD) | 108.59 | 110.15 | .536 |
|  | (11.23) | (9.21) |  |
| Race/Ethnicity |  |  | .827 |
| White | 30 | 18 |  |
| Hispanic | 3 | 2 |  |
| Asian | 4 | 1 |  |
| Black | 15 | 5 |  |
| Other | 2 | 1 |  |

[a]Statistical significant of t-test or chi-square, as appropriate.

Follow-up analyses, evaluated in separate logistic regression models, were conducted for individual components of the Saccadic Impairment scores. As shown in Table 7, greater Saccadic MDC Variability was significantly predictive of prior history of mild TBI (Wald=4.24, p<0.05). Each Saccadic MDC Variability Impairment point was associated with a 266% greater likelihood of Mild TBI. A non-significant trend was also present for Saccadic MDC RT (Wald=3.14, p=0.08), with each Saccadic MDC RT Impairment point associated with a 231% greater likelihood of Mild TBI. By comparison, Global Cognition, from the conventional neuropsychological battery, was not significantly related to Mild TBI history (Wald=0.72, p=0.40). Follow-up analyses evaluating the predictive value of individual neuropsychological domain scores (Motor, Speed, Attention, Executive Functions, and Memory) were also non-significant.

TABLE 7

Value of BEAM Saccadic Impairment Scores for
Predicting Presence of Mild TBI History

| Variable | Wald | Exp(B) |
|---|---|---|
| Saccadic Impairment | 3.88* | 1.21 |
| DCW RT | 1.07 | 1.69 |
| NDC RT | 0.00 | 1.00 |
| MDC RT | 3.14^ | 2.31 |
| UCG RT | 0.50 | 1.44 |
| UC RT | 2.31 | 2.19 |
| DCW Variability | 0.38 | 0.73 |
| NDC Variability | 2.38 | 2.07 |
| MDC Variability | 4.24* | 2.66 |
| UCG Variability | 0.28 | 1.31 |
| UC Variability | 2.56 | 2.23 |

Note:
Univariate logistic regressions with df = 1.
^p < 0.1;
*p < .05.

Results—Number of Mild TBIs: In a linear regression model, higher Saccadic Impairment scores were significantly predictive of greater number of Mild TBIs ($\beta=0.37$, p<0.001, $r^2=0.14$). Separate models predicting number of mild TBIs from Manual Impairment ($\beta=-0.03$, p=0.80), Saccadic Commission Errors ($\beta=0.09$, p=0.41), Saccadic Omission Errors ($\beta=0.06$, p=0.58), Manual Commission Errors ($\beta=0.18$, p=0.11), Manual Omission Errors ($\beta=0.04$, p=0.70), and Ocular-Manual Quotient ($\beta=0.17$, p=0.12) were non-significant. Follow-up analyses were conducted using separate linear regression models for individual components of the Saccadic RT Impairment scores. As shown in Table 8, higher Saccadic RT and Variability scores for each of the MDC, UCG, and UC were significantly predictive of greater number of Mild TBIs. By comparison, Global Cognition, from the conventional neuropsychological battery, was not significantly related to number of Mild TBIs ($\beta=-0.01$, p=0.97). Follow-up analyses evaluating the predictive value of individual neuropsychological domain scores (Motor, Speed, Attention, Executive Functions, and Memory) were also non-significant.

TABLE 8

Value of BEAM Saccadic RT Impairment Scores
for Predicting Number of Mild TBIs

| Variable | Standardized $\beta$ | $r^2$ |
|---|---|---|
| Saccadic RT Impairment | .37*** | .14 |
| DCW RT | .05 | .00 |
| NDC RT | .08 | .01 |
| MDC RT | .32** | .10 |
| UCG RT | .44*** | .19 |
| UC RT | .26* | .07 |

TABLE 8-continued

Value of BEAM Saccadic RT Impairment Scores
for Predicting Number of Mild TBIs

| Variable | Standardized β | r² |
|---|---|---|
| DCW Variability | −.11 | .01 |
| NDC Variability | .07 | .01 |
| MDC Variability | .26* | .07 |
| UCG Variability | .23* | .05 |
| UC Variability | .35** | .13 |

Note:
Univariate logistic regressions with df = 1, 79.
^p < 0.1;
*p < .05;
**p < .01;
***p < .001.

Conclusions: Metrics determined by the method of Example 1 (BEAM) were uniquely predictive of presence of mild TBI history and number of mild TBIs. By contrast, scores from the conventional neuropsychological battery were not predictive of prior history or number of mild TBIs. Notably, the ability of Ocular-Manual Quotient to predict mild TBI history demonstrates the value of multiple-sensor measurement as implemented using this technology (in this example, concurrent measurement and analysis of eye and manual movement). Additionally, whereas the diagnostic algorithms utilized in this example were consider equally (e.g., unweighted) in order to provide an unbiased evaluation of the robustness of the approach, continued improvement of the diagnostic classification algorithm can be achieved using a weighted diagnostic algorithm in further research.

Example 4

Evaluation of BEAM as a Measure of Neurocognitive Status

Methods: Analyses were performed to evaluate the use of BEAM RT to detect neurocognitive status as defined by a comprehensive battery of conventional neuropsychological tests. The study followed the BEAM procedures as described in Examples 1, 2, and 3 (including the same healthy control group and mild TBI groups used in Example 3).

Results: As shown in Table 9, a broad range of BEAM metrics were associated with Global Cognition, including saccadic metrics, manual metrics, and a combined saccadic-manual metric (Ocular-Manual Quotient). Individual BEAM metrics (Saccadic and Manual RT Impairment, Omission, and Commission scores) were differentially associated with individual neuropsychological domains. Motor function was most strongly correlated with Ocular-Manual Quotient and Manual RT Impairment, whereas Speed was most strongly related to Ocular-Manual Quotient, Attention was most strongly associated with Manual Commissions, and Executive functions were most strongly related to Saccadic Commissions. Memory, which is not a primary construct assessed by the BEAM, was less strongly and less consistently related to BEAM metrics. Examining relationships to psychiatric variables, greater Manual RT Impairment was strongly associated with greater depression, and both Manual RT Impairment and the Ocular-Manual Quotient were associated with traumatic stress. No saccadic scores were associated with psychiatric status. By comparison, Global Cognition and the Executive and Memory domains of the conventional neuropsychological battery were associated with traumatic stress.

TABLE 9

Cognitive and Psychiatric Correlates of BEAM Score and Conventional Neuropsychological Domains

| Variable | Global Cognition | Motor | Speed | Attention | Executive | Memory | Depression | Traumatic Stress |
|---|---|---|---|---|---|---|---|---|
| Saccadic RT Impairment Score | .28* | .16 | .26* | .15 | .28* | .16 | −.18 | .14 |
| Saccadic Omissions† | .28** | .15 | .23* | .18 | .24* | .15 | .06 | .16 |
| Saccadic Commissions† | .33** | .13 | .23* | .12 | .34** | .22* | .16 | −.08 |
| Manual RT Impairment Score | .36*** | .31** | .19^ | .24* | .30** | .20^ | .29* | .47*** |
| Manual Omissions† | .37*** | .26* | .27* | .32** | .32** | .15 | −.10 | .05 |
| Manual Commissions† | .31** | .02 | .19^ | .34** | .29** | .22* | .06 | .05 |
| Ocular-Manual Quotient | .30** | .31** | .20^ | .07 | .26* | .16 | −.17 | −.34* |
| Depression | −.05 | −.20 | .00 | −.10 | .21 | −.01 | 1.00 | .64*** |
| Traumatic Stress | .28* | .02 | .18 | .10 | .35** | .30* | .64*** | 1.00 |

Note:
^p < 0.1;
*p < .05;
**p < .01;
***p < .001.
Variables denoted with † indicate non-parametric Spearman correlation; all other results represent Pearson correlations.

Conclusions: The results obtained from the present procedure provide strong evidence for convergent validity of BEAM methods for detection of neurocognitive impairments. In addition to their sensitivity to global cognition, BEAM variables were related to all domains assessed in the comprehensive conventional neuropsychological evaluation (executive functions, speed, motor function, attention, and memory). Evidence for divergent validity was provided by weaker relationships of BEAM metrics to Memory. Furthermore, the differential patterns of relationships between BEAM metrics and traditional neuropsychological domains provides evidence that impairment on individual cognitive domains may be detected and differentiated through an examination of an individual's pattern of BEAM scores. Notably, the value of Ocular-Manual Quotient in assessing global cognition, motor function, and executive functions provides further evidence for the value of multiple-sensor measurement as implemented in this technology. Regarding psychiatric factors, these findings demonstrate that saccadic scores are uniquely resistant to influence from depression and traumatic stress, as compared to a conventional neuropsychological battery. In combination with the results from Example 3, it can be seen that a comparison of BEAM Saccadic vs. Manual RT Impairment scores can be used to assist with differentiating between TBI and psychiatric conditions.

Example 5

Embedded Metrics to Evaluate Validity of BEAM Performance

Methods: Fifty Additional subjects were obtained for an experimental study to identify BEAM metrics and cutoffs that can be used to evaluate the validity of an individual subject's performance. These "Malingering Study" Subjects were randomized to groups that were either instructed to A) provide their best possible performance, or B) attempt to simulate the effects of brain injury on testing. Each subject them completed the BEAM as described in Example 1. Examiners were blinded to subject group assignment. Receiver operating characteristic (ROC) curves and logistic regression models were used to identify BEAM metrics with the greatest potential to detect simulated impairment. Optimal cutoff scores that demonstrated the best sensitivity while maintaining specificity >90% were determined. These empirically-derived cutoffs were then applied to the combined Healthy Control and Mild TBI group data described in examples 2, 3, and 4 for cross-validation within another "best effort" sample.

Results: Demographics for the Malingering Study participant groups are presented in Table 10. Within the Malingering Study sample, overall manual RT variability, saccadic commissions, DCW trial type saccadic RT variability, and manual omissions demonstrated the best classification accuracy. Cutoffs for these variables were then adjusted to achieve 95% specificity within the combined Healthy Control and Mild TBI groups. These analyses demonstrated that for manual RT a cutoff of 0.127 sec achieved sensitivity of 73.9% and specificity of 95.1%. Additionally, for saccadic commissions a cutoff of 47.88% achieved sensitivity of 75% and specificity of 96.3%. The remaining variables failed to achieve sensitivity >60% with specificity >95% in the combined Healthy Control and Mild TBI sample.

Conclusions: These results provide strong evidence that embedded BEAM metrics can be used to assess performance validity with high levels of specificity and sensitivity. These metrics may be used in place of, or as a supplement to, the lengthy and cumbersome standalone tests that are commonly used to assess performance and symptom validity in conventional neuropsychological assessments.

TABLE 10

Participant Demographics - Malingering Study Groups

|  | Control | Simulated TBI | $p^a$ |
|---|---|---|---|
| N | 26 | 24 |  |
| Female | 53.80% | 62.50% | .545 |
| Mean age in years (SD) | 28.35 | 28.63 | .920 |
|  | (10.49) | (8.87) |  |

TABLE 10-continued

Participant Demographics - Malingering Study Groups

|  | Control | Simulated TBI | $p^a$ |
|---|---|---|---|
| Mean years education (SD) | 16.69 | 16.92 | .671 |
|  | (1.67) | (2.041) |  |
| Mean estimated premorbid IQ (SD) | 114.54 | 115.71 | .561 |
|  | (5.69) | (8.10) |  |
| Race/Ethnicity |  |  | .132 |
| White | 21 | 16 |  |
| Hispanic | 0 | 1 |  |
| Asian | 1 | 5 |  |
| Black | 4 | 1 |  |
| Other | 0 | 1 |  |

$^a$Statistical significant of t-test or chi-square, as appropriate.

Example 6

Functional Magnetic Resonance Imaging of BEAM

Figure 6:
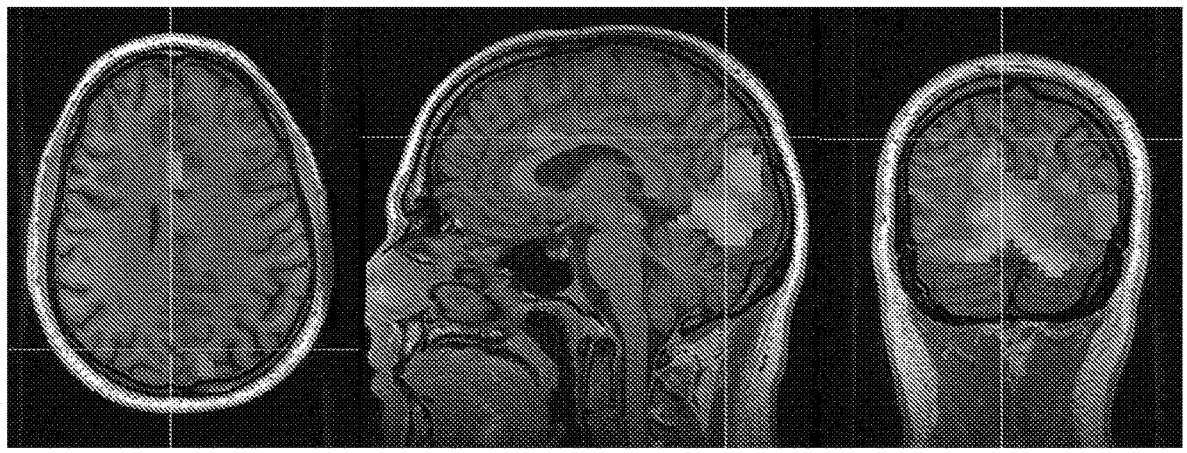
FIG. 6 shows preliminary images derived from developmental scans utilizing combined eye tracking and fMRI.

Developmental fMRI imaging of the USUHS eye tracking system is contemplated. As shown in FIG. 6, patterns of neural activation elicited by the task are consistent with the processes of interest.

FIG. 6 shows preliminary images derived from developmental scans utilizing the combined eye tracking and fMRI. BOLD fMRI activation from a single individual during MDC trials. Prominent areas of activation with likely processing include broad occipital cortex (general visual processing), dorsal cingulate gyms (inhibition/performance monitoring), and superior colliculi (execution of eye movements).

Embodiments of the present invention have been described in the general context of method steps which may be implemented in one embodiment by a program product including machine-executable instructions, such as program code, for example in the form of program modules executed by machines in networked environments. Generally, program modules include routines, programs, logics, objects, components, data structures, etc. that perform particular tasks or implement particular abstract data types. Machine-executable instructions, associated data structures, and program modules represent examples of program code for executing steps of the methods disclosed herein. The particular sequence of such executable instructions or associated data structures represent examples of corresponding acts for implementing the functions described in such steps.

As previously indicated, embodiments of the present invention may be practiced in a networked environment using logical connections to one or more remote computers having processors. Those skilled in the art will appreciate that such network computing environments may encompass many types of computers, including personal computers, hand-held devices, multi-processor systems, microprocessor-based or programmable consumer electronics, network PCs, minicomputers, mainframe computers, and so on. Embodiments of the invention also may be practiced in distributed and cloud computing environments where tasks are performed by local and remote processing devices that are linked, by hardwired links, by wireless links or by a combination of hardwired or wireless links, through a communications network. In a distributed computing environment, program modules may be located in both local and remote memory storage devices.

Although the discussions above may refer to a specific order and composition of method steps, it is understood that the order of these steps may differ from what is described. For example, two or more steps may be performed concurrently or with partial concurrence. Also, some method steps that are performed as discrete steps may be combined, steps being performed as a combined step may be separated into discrete steps, the sequence of certain processes may be reversed or otherwise varied, and the nature or number of discrete processes may be altered or varied. The order or sequence of any element or apparatus may be varied or substituted according to alternative embodiments. Accordingly, all such modifications are intended to be included within the scope of the present invention. Such variations will depend on the software and hardware systems chosen and on designer choice. It is understood that all such variations are within the scope of the invention. Likewise, software and web implementations of the present invention could be accomplished with standard programming techniques with rule based logic and other logic to accomplish the various database searching steps, correlation steps, comparison steps and decision steps.

While the foregoing description illustrates specific embodiments and optional features, the invention is not limited to specific embodiments, and includes all permutations and combinations of the features, aspects, and embodiments described herein. Thus, all permutations and combinations of the disclosed features aspects, and embodiments are considered within the scope of the invention.

The invention claimed is:

1. A system comprising a processor and program code which, when executed by the processor, configures the system to conduct an assessment of the neurological and/or psychological status of a subject, comprising:
    displaying a plurality of visual tests to a human subject, wherein each visual test comprises a visual target signal being a displayed command for an eye movement, and one or more of the visual tests further comprises a visual cue signal displayed prior to the visual target signal, wherein the visual cue signal comprises a directional cue signal or a misdirectional cue signal;
    following the display of each visual target signal, detecting, via a sensor and the processor, an involuntary eye movement of the subject and a responsive eye movement of the subject;
    assessing the neurological and/or psychological status of the subject to determine the presence of neurocognitive disorder in the subject, wherein the presence is determined based on the correctness and timing of the detected responsive eye movements with regard to the commanded movements associated with each visual test, wherein the correctness of the responsive eye movement is determined with reference to a correlation of the responsive eye movement with the visual target signal of the visual test, as modified by any visual cue signal of the visual test; and
    automatically providing an output to aid interpretation of results of the assessment selected from the group consisting of numerical output, graphical output, visual output, and textual output,
    wherein the visual cue signal is displayed for from about 50 ms to about 500 ms before the visual target signal, and
    wherein, in one or more of the visual tests, the visual target signal is further associated with a commanded body part movement of a body part other than the eye of the subject, and the detecting following the display of each visual target signal further comprises detecting a responsive body part movement of the body part other than the eye of the subject.

2. The system of claim 1, further comprising detecting fixation of the subject's gaze on the visual target signal of the visual test.

3. The system of claim 1, further comprising moving the visual target signal and detecting whether the subject's eye movement tracks the movement of the visual target signal.

4. The system of claim 1, wherein the detected eye movement comprises horizontal movement, vertical movement, dilation or constriction.

5. The system of claim 1, wherein the assessment is further based on one or more of the latency of the detected movements, the correctness of the detected eye movements with regard to the displayed commands for the eye movements, the correctness of the detected body part movements with regard to the commanded body part movements, and the coordination between the detected eye and body part movements.

6. The system of claim 1, wherein the program code further configures the system during the assessment to automatically recalibrate to compensate for changes in head position during the assessment.

7. The system of claim 1, wherein the program code further configures the system to monitor the subject's readiness to respond to a visual test.

8. The system of claim 1, wherein the program code configures the system to detect a non-responsive eye movement, wherein the assessment is further based on the non-responsive eye movement.

9. The system of claim 1, wherein the sensor is configured to detect one or more of vertical movement of the eye, horizontal movement of the eye, dilation of the pupil, or constriction of the pupil.

10. The system of claim 1, further comprising a sensor configured to detect the movement of the body part.

11. A non-transitory computer-readable medium comprising program code which, when executed, configures a system to:
    display a plurality of visual tests to a human subject, wherein each visual test comprises a visual target signal being a displayed command for an eye movement, and one or more of the visual tests further comprises a visual cue signal displayed prior to the visual target signal, wherein the visual cue signal comprises a directional cue signal or a misdirectional cue signal;
    following the display of each visual target signal, detect, via a sensor and a processor, an involuntary eye movement of the subject and a responsive eye movement of the subject; and
    assess the neurological and/or psychological status of the subject to determine the presence of neurocognitive disorder in the subject, wherein the presence is determined based on the correctness and timing of the detected responsive movements with regard to the commanded movements associated with each visual test, wherein the correctness of the responsive eye movement is determined with reference to a correlation of the responsive eye movement with the visual target signal of the visual test, as modified by any visual cue signal of the visual test; and
    automatically provide an output to aid interpretation of results of the assessed neurological and/or psychological status of the subject selected from the group consisting of numerical output, graphical output, visual output, and textual output, wherein, in one or more of the visual tests, the visual target signal is further associated with a commanded body part movement of a body part other than the eye of the subject, and the detecting following the display of each visual target signal further comprises detecting a responsive body part movement of the body part other than the eye of the subject.

12. A method for conducting an assessment of the neurological and/or psychological status or neurocognitive function of a human subject, comprising:

displaying, on an electronic screen, a plurality of visual tests to a human subject, wherein each visual test comprises a visual target signal being a displayed command for an eye movement, and one or more of the visual tests further comprises a visual cue signal displayed prior to the visual target signal, wherein the visual cue signal comprises a directional cue signal or a misdirectional cue signal;

following the display of each visual target signal, detecting, via a sensor and a processor, an involuntary eye movement of the subject and a responsive eye movement of the subject; and assessing the neurological and/or psychological status or neurocognitive function of the subject to determine the presence of neurocognitive disorder in the subject, wherein the presence is determined based on the correctness and timing of the detected responsive movements with regard to the commanded movements associated with each visual test, wherein the correctness of the responsive eye movement is determined with reference to a correlation of the responsive eye movement with the visual target signal of the visual test, as modified by any visual cue signal of the visual test; and automatically providing an output to aid interpretation of results of the assessment selected from the group consisting of numerical output, graphical output, visual output, and textual output, wherein the visual target signal is displayed for from about 50 ms to about 500 ms, and wherein, in one or more of the visual tests, the visual target signal is further associated with a commanded body part movement of a body part other than the eye of the subject, and the detecting following the display of each visual target signal further comprises detecting a responsive body part movement of the body part other than the eye of the subject.

13. The system of claim 1, wherein the assessment further comprises:
assessing the neurological and/or psychological status of the subject based on the latency of the detected responsive movements with regard to the commanded movements associated with each visual test.

14. The system of claim 1, wherein the assessment further comprises:
comparing metrics representing the subject's performance to the subject's prior performance to facilitate tracking changes of performance relevant to medical care of the subject.

15. The system of claim 7, wherein the program code further configures the system to pause an assessment, recalibrate, provide instructions to the subject, and/or issue a warning to the subject.

16. The system of claim 1, wherein the visual cue signal provides information about a timing and a location of the visual target signal.

17. The system of claim 1, wherein the visual cue signal provides information about the displayed command for an eye movement.

18. The system of claim 1, wherein the visual cue signal is displayed from about 150 ms to about 300 ms before the visual target signal.

19. The system of claim 1, wherein the neurocognitive disorder is concussion.

20. The system of claim 1, wherein the neurocognitive disorder is brain injury.

21. The system of claim 1, wherein the neurocognitive disorder is traumatic brain injury.

22. The system of claim 1, wherein the timing of the detected responsive eye movements of the subject in response to the visual cue signal is indicative of a reaction of the subject to the directional cue signal or the misdirectional cue signal.

23. The non-transitory computer-readable medium of claim 11, wherein the timing of the detected responsive eye movements of the subject in response to the visual cue signal is indicative of a reaction of the subject to the directional cue signal or the misdirectional cue signal.

24. The method of claim 12, wherein the timing of the detected responsive eye movements of the subject in response to the visual cue signal is indicative of a reaction of the subject to the directional cue signal or the misdirectional cue signal.

* * * * *